(12) United States Patent
Fortson et al.

(10) Patent No.: US 10,772,621 B2
(45) Date of Patent: Sep. 15, 2020

(54) SUTURE MANAGEMENT DEVICES, METHODS, AND SYSTEMS

(71) Applicant: Abbott Cardiovascular Systems, Inc., Santa Clara, CA (US)

(72) Inventors: Aaron M. Fortson, Fremont, CA (US); David J. Milazzo, Santa Clara, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 301 days.

(21) Appl. No.: 15/887,526

(22) Filed: Feb. 2, 2018

(65) Prior Publication Data

US 2019/0239871 A1    Aug. 8, 2019

(51) Int. Cl.
| | | |
|---|---|---|
| *A61B 17/04* | (2006.01) | |
| *A61B 17/06* | (2006.01) | |
| *A61B 46/23* | (2016.01) | |
| *A61B 17/00* | (2006.01) | |
| *A61B 90/00* | (2016.01) | |
| *A61B 90/92* | (2016.01) | |

(52) U.S. Cl.
CPC ...... *A61B 17/0482* (2013.01); *A61B 17/0467* (2013.01); *A61B 17/0483* (2013.01); *A61B 17/0485* (2013.01); *A61B 17/06061* (2013.01); *A61B 46/23* (2016.02); *A61B 90/92* (2016.02); *A61B 2017/00477* (2013.01); *A61B 2017/00862* (2013.01); *A61B 2017/0474* (2013.01); *A61B 2090/0807* (2016.02)

(58) Field of Classification Search
CPC ............ A61B 17/0482; A61B 17/0483; A61B 17/0485; A61B 17/06061; A61B 46/23; A61B 90/90; A61B 90/92; A61B 90/94; A61B 2090/0807; A61B 2090/0808; A61B 2090/0809; A61B 2017/0474
See application file for complete search history.

(56) References Cited

U.S. PATENT DOCUMENTS

| | | |
|---|---|---|
| 3,328,876 A | 7/1967 | Hoppe |
| 3,372,477 A | 3/1968 | Hoppe |
| 3,380,448 A | 4/1968 | Sadove et al. |
| 3,625,556 A | 12/1971 | Stromberg |

(Continued)

FOREIGN PATENT DOCUMENTS

| | | |
|---|---|---|
| DE | 9112301 | 1/1992 |
| DE | 9214580 | 4/1994 |

(Continued)

OTHER PUBLICATIONS

U.S. Appl. No. 10/004,817, Dec. 18, 2002, OA.

(Continued)

*Primary Examiner* — Melanie R Tyson
(74) *Attorney, Agent, or Firm* — Workman Nydegger; Randy Shen

(57) ABSTRACT

A suture management member including a body being elongate in a first direction and having a suture-receiving recess in a second direction transverse to the first direction. The suture-receiving recess extends partially through the body and separates the body into a first portion and a second portion. The first portion is being biased towards the second portion to securely retaining a suture within the suture-receiving recess.

17 Claims, 17 Drawing Sheets

(56) References Cited

U.S. PATENT DOCUMENTS

| | | |
|---|---|---|
| 3,752,516 A | 8/1973 | Mumma |
| 3,840,017 A | 10/1974 | Violante |
| 4,246,698 A | 1/1981 | Lasner et al. |
| 4,369,787 A | 1/1983 | Lasner et al. |
| 4,423,837 A | 1/1984 | Clements |
| 4,527,331 A | 7/1985 | Lasner et al. |
| 4,602,635 A | 7/1986 | Mulhollan et al. |
| 4,641,652 A | 2/1987 | Hutterer et al. |
| 4,662,068 A | 5/1987 | Polonsky |
| 4,841,888 A | 6/1989 | Mills et al. |
| 4,845,851 A | 7/1989 | Warthen |
| 4,957,498 A | 9/1990 | Caspari et al. |
| 4,961,741 A | 10/1990 | Hayhurst |
| 5,059,201 A | 10/1991 | Asnis |
| 5,133,723 A | 7/1992 | Li et al. |
| 5,176,691 A | 1/1993 | Pierce |
| 5,176,695 A | 1/1993 | Dulebohn |
| 5,242,459 A | 9/1993 | Buelna |
| 5,269,791 A | 12/1993 | Mayzels et al. |
| 5,292,327 A | 3/1994 | Dodd et al. |
| 5,304,190 A | 4/1994 | Reckelhoff et al. |
| 5,312,423 A | 5/1994 | Rosenbluth et al. |
| 5,342,459 A | 8/1994 | Klemp et al. |
| 5,403,330 A | 4/1995 | Tuason |
| 5,405,351 A | 4/1995 | Kinet et al. |
| 5,405,354 A | 4/1995 | Sarrett |
| 5,417,699 A | 5/1995 | Klein et al. |
| 5,423,837 A | 6/1995 | Mericle et al. |
| 5,462,562 A | 10/1995 | Elkus |
| 5,520,702 A | 5/1996 | Sauer et al. |
| 5,527,322 A | 6/1996 | Klein et al. |
| 5,545,178 A | 8/1996 | Kensey et al. |
| 5,549,617 A | 8/1996 | Green et al. |
| 5,549,618 A | 8/1996 | Fleenor et al. |
| 5,565,122 A | 10/1996 | Zinnbauer et al. |
| 5,585,122 A | 12/1996 | Drum et al. |
| 5,643,289 A | 7/1997 | Sauer et al. |
| 5,649,939 A | 7/1997 | Reddick |
| 5,662,681 A | 9/1997 | Nash et al. |
| 5,669,917 A | 9/1997 | Sauer et al. |
| 5,681,334 A | 10/1997 | Evans et al. |
| 5,704,943 A | 1/1998 | Yoon et al. |
| 5,746,752 A | 5/1998 | Burkhart |
| 5,797,928 A | 8/1998 | Kogasaka |
| 5,797,929 A | 8/1998 | Andreas et al. |
| 5,830,234 A | 11/1998 | Wojciechowicz et al. |
| 5,860,993 A | 1/1999 | Thompson et al. |
| 5,879,371 A | 3/1999 | Gardiner et al. |
| 5,997,555 A | 12/1999 | Kontos |
| 6,004,295 A | 12/1999 | Langer et al. |
| 6,007,544 A | 12/1999 | Kim |
| 6,045,570 A | 4/2000 | Epstein et al. |
| 6,051,004 A | 4/2000 | Gill |
| 6,077,277 A | 6/2000 | Mollenauer et al. |
| 6,077,279 A | 6/2000 | Kontos |
| 6,090,063 A | 7/2000 | Makower et al. |
| 6,132,439 A | 10/2000 | Kontos |
| 6,171,317 B1 | 1/2001 | Jackson et al. |
| 6,254,620 B1 | 7/2001 | Koh et al. |
| 6,261,272 B1 | 7/2001 | Gross et al. |
| 6,488,690 B1 | 12/2002 | Morris et al. |
| 6,527,785 B2 | 3/2003 | Sancoff et al. |
| 6,554,845 B1 | 4/2003 | Fleenor |
| 6,620,185 B1 | 9/2003 | Harvie et al. |
| 6,733,509 B2 | 5/2004 | Nobles et al. |
| 6,746,457 B2 | 6/2004 | Dana et al. |
| 6,860,890 B2 | 3/2005 | Bachman et al. |
| 7,094,246 B2 | 8/2006 | Anderson et al. |
| 7,147,646 B2 | 12/2006 | Dana et al. |
| 7,842,051 B2 | 11/2010 | Dana et al. |
| 7,918,867 B2 | 4/2011 | Dana et al. |
| 7,992,571 B2 | 8/2011 | Gross et al. |
| 8,088,143 B2 | 1/2012 | Akerfeldt |
| 8,197,497 B2 | 6/2012 | Nobles et al. |
| 8,211,123 B2 | 7/2012 | Gross et al. |
| 8,480,691 B2 | 7/2013 | Dana et al. |
| 8,585,720 B2 | 11/2013 | Gross et al. |
| 9,320,515 B2 | 4/2016 | Dana et al. |
| 9,750,494 B2 | 9/2017 | Gross et al. |
| 10,143,463 B2 | 12/2018 | Dana et al. |
| 2004/0087978 A1 | 5/2004 | Velez |
| 2008/0065113 A1 | 3/2008 | Smith |
| 2012/0053629 A1* | 3/2012 | Reiser ............... A61B 17/0401 606/232 |
| 2015/0245901 A1* | 9/2015 | Dougherty ......... A61B 17/0483 606/232 |
| 2016/0317144 A1* | 11/2016 | Popovici ............ A61B 17/0469 |
| 2017/0319197 A1 | 11/2017 | Gross et al. |

FOREIGN PATENT DOCUMENTS

| | | |
|---|---|---|
| EP | 0669103 | 9/1999 |
| WO | WO 94/08515 | 4/1994 |
| WO | WO 95/32669 | 12/1995 |
| WO | WO 00/69342 | 11/2000 |
| WO | WO 02/15795 | 2/2002 |
| WO | WO 03/049621 | 6/2003 |
| WO | WO 03/059174 | 7/2003 |

OTHER PUBLICATIONS

U.S. Appl. No. 10/004,817, Jul. 28, 2003, Notice of Allowance.
U.S. Appl. No. 10/004,817, Feb. 4, 2004, Notice of Allowance.
U.S. Appl. No. 10/027,681, Jun. 2, 2003, Office Action.
U.S. Appl. No. 10/027,681, Dec. 8, 2003, Office Action.
U.S. Appl. No. 10/027,681, May 28, 2004, Office Action.
U.S. Appl. No. 10/027,681, Oct. 23, 2006, Office Action.
U.S. Appl. No. 10/027,681, Apr. 17, 2007, Office Action.
U.S. Appl. No. 10/027,681, Oct. 30, 2007, Office Action.
U.S. Appl. No. 10/027,681, May 27, 2008, Office Action.
U.S. Appl. No. 10/027,681, Dec. 23, 2008, Office Action.
U.S. Appl. No. 10/027,681, Jul. 8, 2009, Office Action.
U.S. Appl. No. 10/027,681, Feb. 17, 2010, Office Action.
U.S. Appl. No. 10/027,681, Aug. 16, 2010, Office Action.
U.S. Appl. No. 10/027,681, Jan. 19, 2011, Office Action.
U.S. Appl. No. 10/027,681, Feb. 3, 2012, Office Action.
U.S. Appl. No. 10/027,681, Apr. 5, 2012, Notice of Allowance.
U.S. Appl. No. 10/324,730, Mar. 27, 2006, Office Action.
U.S. Appl. No. 10/324,730, Aug. 8, 2006, Office Action.
U.S. Appl. No. 10/324,730, Jan. 29, 2007, Office Action.
U.S. Appl. No. 10/324,730, Aug. 30, 2007, Notice of Allowance.
U.S. Appl. No. 10/324,730, Aug. 19, 2008, Office Action.
U.S. Appl. No. 10/324,730, Oct. 30, 2009, Notice of Allowance.
U.S. Appl. No. 10/324,730, Mar. 23, 2010, Notice of Allowance.
U.S. Appl. No. 10/324,730, Sep. 22, 2010, Notice of Allowance.
U.S. Appl. No. 10/661,155, Aug. 31, 2005, Office Action.
U.S. Appl. No. 10/661,155, Feb. 23, 2006, Notice of Allowance.
U.S. Appl. No. 10/860,443, May 17, 2006, Office Action.
U.S. Appl. No. 10/860,443, Oct. 2, 2006, Notice of Allowance.
U.S. Appl. No. 11/461,243, Apr. 29, 2009, Office Action.
U.S. Appl. No. 11/461,243, Oct. 21, 2009, Office Action.
U.S. Appl. No. 11/461,243, Mar. 15, 2010, Office Action.
U.S. Appl. No. 11/461,243, Jul. 28, 2010, Notice of Allowance.
U.S. Appl. No. 11/465,035, Nov. 28, 2008, Office Action.
U.S. Appl. No. 11/465,035, Mar. 4, 2010, Office Action.
U.S. Appl. No. 11/465,035, Jun. 22, 2010, Office Action.
U.S. Appl. No. 11/465,035, Mar. 31, 2011, Notice of Allowance.
U.S. Appl. No. 12/914,658, Nov. 19, 2012, Office Action.
U.S. Appl. No. 12/914,658, Mar. 7, 2013, Notice of Allowance.
U.S. Appl. No. 13/539,095, Dec. 6, 2012, Office Action.
U.S. Appl. No. 13/539,095, Jul. 10, 2013, Notice of Allowance.
U.S. Appl. No. 13/936,593, Jul. 27, 2015, Office Action.
U.S. Appl. No. 13/936,593, Jan. 12, 2016, Notice of Allowance.
U.S. Appl. No. 14/083,173, Apr. 6, 2016, Office Action.
U.S. Appl. No. 14/083,173, Oct. 18, 2016, Office Action.
U.S. Appl. No. 14/083,173, Mar. 6, 2017, Notice of Allowance.
U.S. Appl. No. 14/083,173, Jul. 3, 2017, Notice of Allowance.
U.S. Appl. No. 15/137,547, Apr. 9, 2018, Office Action.
U.S. Appl. No. 15/137,547, Aug. 1, 2018, Notice of Allowance.

(56) References Cited

OTHER PUBLICATIONS

U.S. Appl. No. 15/660,478, Feb. 7, 2019, Office Action.
U.S. Appl. No. 15/660,478, Aug. 7, 2019, Office Action.
U.S. Appl. No. 15/660,478, Oct. 18, 2019, Notice of Allowance.
U.S. Appl. No. 13/769,015, May 18, 2015, Office Action.
U.S. Appl. No. 13/769,015, Nov. 12, 2015, Office Action.
U.S. Appl. No. 13/769,015, Jan. 29, 2016, Office Action.
U.S. Appl. No. 13/769,015, Mar. 21, 2016, Office Action.
U.S. Appl. No. 13/769,015, Sep. 15, 2016, Office Action.
U.S. Appl. No. 13/769,015, Dec. 20, 2016, Office Action.

* cited by examiner

SUTURE MANAGEMENT DEVICES, METHODS, AND SYSTEMS

CROSS-REFERENCE TO RELATED APPLICATIONS

NA

BACKGROUND OF THE INVENTION

1. The Field of the Invention

The present invention relates generally to surgical devices and methods. More particularly, the present invention relates to the construction and use of devices for Controlling sutures both before and during a procedure, and subsequently advancing surgical knot(s) to the surgical site.

2. The Relevant Technology

The closing of incision and wounds using suture is a preferred technique of surgeons and many other physicians. While other techniques are now available such as stapling, the use of "tissue glues," and the use of collagen for closing vascular punctures, the use of suture is often preferred because it provides a reliable and tight closure of any wound. Additionally, if a suture is to fail, the surgeon will know immediately, this is unlike many of the other devices listed above which may not fail until sometime after the procedure.

While the suturing of a wound is a relatively straight forward procedure in most open surgical procedures, placement and tying of sutures in laparoscopic and other minimally invasive procedures can be problematic. To provide for suturing under such circumstances, a variety of devices have been developed for the remote placement and tying of suture through cannulas under video observation. Usually, a sliding knot will be formed in a suture loop, a tool known as a "knot pusher," such as that shown in U.S. Pat. No. 5,797,929 the entirety of which is hereby incorporated by reference, is utilized to advance and position the knot and tighten the loop of suture.

Such knot pushing devices may also be utilized in recently developed techniques for the remote suturing of vascular punctures. Punctures may be formed in the femoral or other arteries to provide vascular access for performing angioplasty and other vascular procedures. Such techniques are described in U.S. Pat. Nos. 5,417,699 and 5,527,322, the entireties of which are hereby incorporated by reference. Such methods result in the placement of a suture loop through tissue on opposite sides of the vascular puncture. Two free ends of the suture loop are brought out through a tissue tract leading to the puncture, and the ends may be externally tied by the treating physician.

During some procedures it may be desired to use multiple sutures to close an incision. Managing the suture ends sometimes becomes difficult when multiple suture loops extend across the puncture. A need therefore exists to manage suture during a procedure, and subsequently advance the knots to a surgical site following procedure completion.

BRIEF SUMMARY OF THE INVENTION

The present disclosure describes devices, systems, and methods for managing sutures during a surgical procedure.

In one embodiment, a suture management member includes a body being elongate in a first direction and having a suture-receiving recess. The suture-receiving recess extends partially through the body and separates the body into a first portion and a second portion, with the first portion being biased towards the second portion.

In some embodiments, the body is monolithic, optionally with a lumen extending in the first direction.

In some embodiments, a portion of the body separating the first portion and the second portion is a living hinge.

In some embodiments, the suture-receiving recess includes suture retention features configured to selectively engage and retain a suture disposed within the suture-receiving recess.

In some embodiments, the suture management member includes a groove disposed on an opposite side of the body from the suture-receiving recess. This groove can be concave.

In some embodiments, the suture management member includes a support assembly coupled to the body. This support assembly includes a mounting portion and a securing portion, the mounting portion connecting the support assembly to the body. The securing portion can include two arms that extend from the mounting portion, at least one of the two arms being movable. The two arms can include a fixed arm and a movable arm, the movable arms being biased toward the fixed arm. The two arms can alternatively include a first movable arm and a second movable arm, the first movable arm and the second movable arm being biased towards each other.

In another embodiment, a method for managing a plurality of sutures includes positioning at least two sutures across an incision during pre-close of the incision. Following capture with a suture handling device, the method includes selectively attaching one suture of the at least two sutures to the suture handling device with a suture management member, a portion of the suture handling device resiliently engaging with a portion of the suture management member to retain the one suture. Following capture with another suture handling device, the method includes selectively attaching the other suture of the at least two sutures to the another suture handling device with another suture management member, a portion of the another suture handling device resiliently engaging with a portion of the another suture management member to retain the other suture. Following capture, the method includes selectively positioning each of the suture handling device and the another suture handling device to maintain a positional relationship of the suture handling device and the another suture handling device with the incision during the procedure and before closure of the incision.

In some embodiments, the another suture management member is different from the suture management member. The difference including differences in indicia identifying an order by which the one suture and the other suture are tied.

In some embodiments, the suture management member and the another suture management member include a suture-receiving recess and can be monolithic flexible members.

In some embodiments, the method includes inserting the suture management member in an opening of the suture handling device. The opening is formed in a proximal end of the suture handling device. The resilient engaging of the suture handling device with the suture management member selectively deforms the suture management member to retain the one suture.

In some embodiments, the suture management member surrounds at least a portion of an elongated member of the suture handling device.

In some embodiments, the suture handling device further comprises a cutting member.

In some embodiments, the method includes mounting the surgical management member to a surgical drape on a patient.

In another embodiment, a kit includes a plurality of suture handling devices, each suture handling device comprising an elongate distal end and a proximal end with a through-aperture and a plurality of suture management members each being different, each suture management member being associated with one of the plurality of suture handling devices and being selectively received within the through-aperture.

In some embodiments, the kit includes a plurality of support assemblies, each support assembly being configured to receive one of the plurality of suture handling devices and/or the plurality of suture management members.

Additional features and advantages will be set forth in part in the description that follows or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
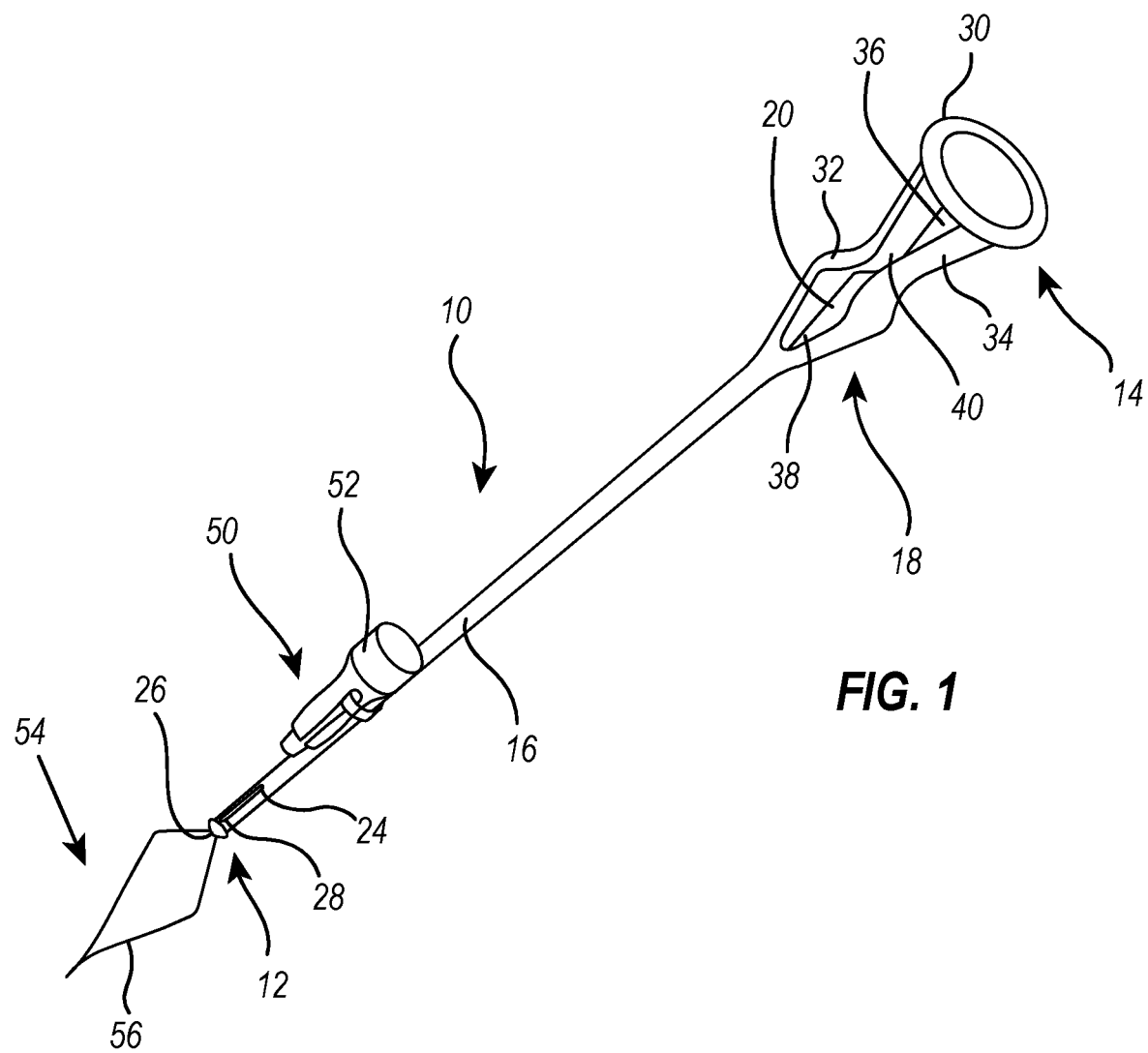
FIG. 1 illustrates a perspective view of an apparatus used to advance a surgical knot along a suture length.

One or more specific embodiments of the present disclosure will be described below. In an effort to provide a concise description of these embodiments, some features of an actual embodiment may be described in the specification.

It should be appreciated that in the development of any such actual embodiment, as in any engineering or design project, numerous embodiment-specific decisions will be made to achieve the developers' specific goals, such as compliance with system-related and business-related constraints, which may vary from one embodiment to another. It should further be appreciated that such a development effort might be complex and time consuming, but would nevertheless be a routine undertaking of design, fabrication, and manufacture for those of ordinary skill having the benefit of this disclosure.

One or more of the embodiments of the present disclosure may generally relate to suture management members and use of same before, after, or as part of a medical procedure, such as a percutaneous intravascular procedure. For instance, certain intravascular procedures utilize a "pre-close" technique where sutures employed to close an opening, or arteriotomy, as a result of a medical procedure, are positioned at the arteriotomy site prior to performing a particular intravascular procedure, such as stenting, etc. The pre-close might include deploying two devices at the arteriotomy site, such that the suture loop extends across the opening or arteriotomy in a crossing fashion or parallel to each other, before placing a sheath through which procedural devices can be advance to perform the desire procedure. The devices used to position the sutures can include, for instance, the Perclose ProGlide Suture Medicated Closure System available from Abbott.

The described suture management members allow a medical professional, such as physician, clinician, etc., to simply and efficiently manage sutures, for instance, that may be placed after or prior to performance of the percutaneous intravascular procedure. The sutures are held by the suture management member(s) until needed to close the opening or arteriotomy. The suture management members can include number, letters, colors, or other information to indicate a sequence of use so that a medical professional can identify which sutures are associated with which suture management member and so manipulate the suture management members, and associated sutures, in a particular order.

While the present disclosure will describe certain suture management members and certain procedures, the devices, systems, and methods described herein may be applicable to other procedures and structures. Additionally, features, functions, and elements described in relation to any embodiment depicted and/or described herein may be combinable with features, functions, and elements described in relation to any other embodiment depicted and/or described herein.

A suture management member may be used in association with devices that advance a knot along a suture and/or cut suture following knot placement. Those devices may include an elongated member that has a distal end and a proximal end. A handle or handle portion may be connected or disposed at a proximal end of the elongated member to allow a user, such as a medical professional, to control movement of the elongated member, and more generally the device itself. In some embodiments, the handle or handle portion may include one or more controls (e.g., a knob, a button, a lever, or other controls) that may move at least part of the device relative to another. For example, the handle or handle portion may include one or more controls for moving a cutting member disposed within the elongated member relative to the elongated member.

When the sutures are managed by the suture management member, either alone or in cooperation with the apparatus used to advance a surgical knot along a suture length, the apparatus and suture management member can be secured relative to the patient through a support assembly. This support assembly selectively attaches to surgical drapes covering the patient, positioning the suture and apparatus for subsequent use without impeding access to the surgical site, while being easily accessible when needed by the medical professional. The support assembly can also include numbers, letters, colors, or other information to indicate a sequence of use so that a medical professional can identify which sutures are associated with which support assembly and so manipulate the support assembly, suture management members, and associated sutures, in a particular order.

FIG. 1 illustrates a schematic representation of an apparatus used to advance a surgical knot along a suture length, such as a suture handling device. The suture handling device, such as a knot pusher 10, is a manual device which can be used by medical professional in any of a variety of surgical procedures where a suture loop has been positioned in tissue to close an incision or wound, or for any other purpose. Once a slidable knot is formed in the suture, the suture handling device is used to engage and advance the knot over a free end of the suture to close the loop. The knot can then be tightened by pulling on the other free end of the suture, and optionally additionally throws may be tied into the suture portions and advanced using this or another knot pusher. Depending upon the particular suture handling device, it can also be used to cut the suture, such as using the suture handling device, knot pusher and suture trimmer 110 illustrated in FIG. 8, and which will be discussed in more detail hereinafter.

Figure 2:
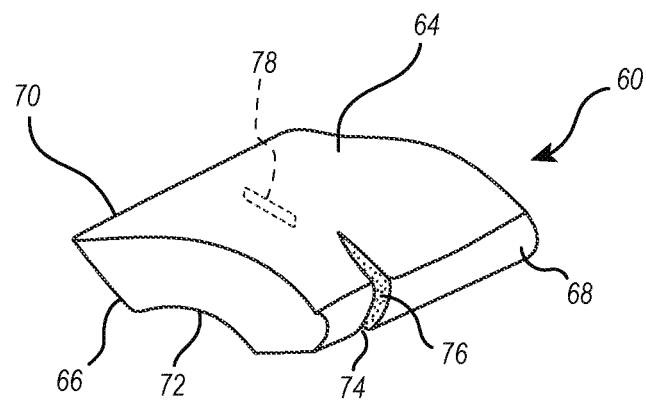
FIG. 2 illustrates a perspective view of a suture management member according one configuration of the present invention.
Figure 3:
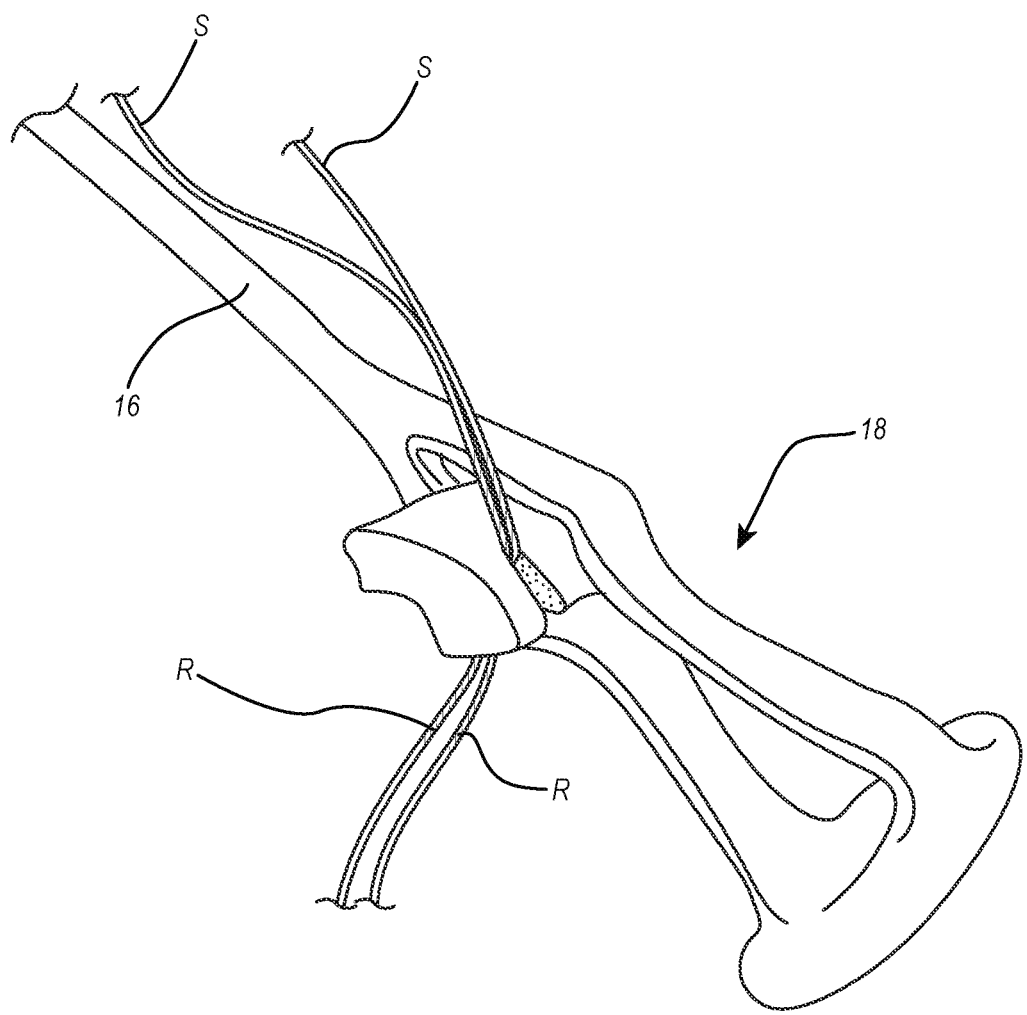
FIG. 3 illustrates a partial perspective view of the suture management member of FIG. 2 with the apparatus of FIG. 1.

As illustrated in FIG. 1, the knot pusher 10, as an example of a suture handling device, has a distal end 12 and a proximal end 14. Proximally extending from the distal end 12 is an elongated portion or member 16, such as a shaft, which extends to a handle portion 18. Openings are formed at the distal end 12 and the handle 18; an opening 20 is formed in the handle 18 and an opening 22 is formed at the distal end 12. The opening 20 accommodates, in one configuration, a portion of a suture management member 60 as illustrated in FIGS. 2 and 3, and which will be described hereinafter. The opening 22 accommodates a portion of a suture snare 50, illustrated attached to the elongated member 16, and includes a proximal slot 24 that communicates with a distally facing aperture 26 through a lumen 28. A portion of the suture snare 50 can be advanced through the proximal slot 24 and lumen 28 to exit aperture 26, as illustrated in FIG. 1. In this orientation, the suture snare 50 is ready to capture suture and draw it through the aperture 26 and lumen 28, so that it extends from the slot 24 ready for tying of a knot and subsequent advancement of the knot to the opening or arteriotomy.

The suture snare 50 includes a housing 52 and a snare 54 extending therefrom. As shown in FIG. 1, the housing 52 has a proximal end and a distal end and is configured to be detachably attached to the elongated member 16 of the knot pusher 10. The snare 54 extends from the distal end of the housing 52. As shown, a distal tip or end portion 56 portion of the snare 54 is configured having a diamond shape, though many other geometric shapes may be utilized and the use of a diamond shaped distal tip shall be considered exemplary. The snare may be constructed of materials such as metal or plastic. Examples of suitable metals are stainless steel, copper, steel, titanium, platinum or nickel-titanium. Alternatively, a non-bio-compatible material may be utilized wherein the non bio-compatible material is then coated with a bio-compatible coating such as gold or silver. Examples of plastics that may be utilized are PVC, polyurethane, and similar plastics. In one embodiment the snare 54 is constructed of nickel-titanium wire. The use of nickel-titanium enables a larger distal tip or end portion 56 than if conventional materials are utilized. Furthermore, the nickel-titanium will not deform or become deformed in normal use because of the shape memory characteristics of the material. The use of a larger distal tip or end portion on the snare provides for easier loading of the sutures therein.

With continued reference to FIG. 1, the handle portion 18 extends from a proximal end of the elongated member 16 in a bifurcated manner, with a proximal enlarged portion 30 and two legs 32 and 34. The legs 32 and 34 form the opening 20 that has a first enlarged opening 36 separated from a second enlarged opening 38 by a narrow region or gap 40. The legs 32 and 34 form a grasping portion of the handle portion 18, with recesses 42, 44 and raised portions 46, 48 that a medical professional can use to control the knot pusher 10. As illustrated in FIG. 1, the legs 32 and 34 are mirror images of each other across a longitudinal axis of the knot pusher 10. However, in alternate configurations, the legs can be different, include similar configurations, or a combination of recesses, raised portions, etc., that are similar and dissimilar.

The opening 20 of the handle portion 18 receives the suture management member 60, as illustrated in FIG. 3. The legs 32 and 34 hold the suture management member 60 so that the sutures S can be held relative to the remainder of the knot pusher 10, and the surgical site, as will be discussed in more detail hereinafter. The suture management member 60 is resiliently deformable to aid with mounting to the handle portion 18 of the knot pusher 10. It can be deformed as it is placed in the opening 20. This deformation can aid with retaining the sutures S to a suture-receiving recess 74 of the suture management member 60 in certain configurations of the suture management member 60.

With reference to FIGS. 2 and 3, the suture management member 60 has a body which includes an outer surface 62 that is generally profiled to cooperate with the legs 32 and 34. The outer surface 62 includes an upper surface 64 and a lower surface 66, with transition end portions 68 and 70 that transition the outer surface 62 from the upper surface 64 to the lower surface 66, and vice versa. The lower surface 66 includes a concave portion or groove 72 that aids with deformation of the suture management member 60 when it is positioned in the opening 20. For instance, since the body of the suture management member 60 is narrower between the upper surface 64 and the lower surface 66 near the concave portion 72, as the suture management member 60 is received by the legs 32 and 34, the body can preferentially deform near the concave portion 72 to aid with holding by the knot pusher 10. While deforming, the resiliency of the body at that narrowed region applies an upward force towards the legs 34 and 34 to maintain contact.

The profile of the body allows a portion of the suture management member 60 to be received in the opening 20 close to the gap 40, in one configuration. The legs 32 and 34 pinch the suture management member 60 near the transition end portion 68 and enhance capture or retaining by the handle portion 18. A similar effect can be achieved if the transition end portion 70 is placed close to a distal end 46 of the second enlarged opening 38, or bifurcation of the legs 32 and 34 at the proximal end of the elongated member 16. Increasing the narrowness of the gap 40 or angular separation of the legs 32 and 34 at the bifurcation, can increase the pinching effect, when coupled with changing the resiliency or deformation characteristics of the suture management member 60. A narrower spacing between legs 32 and 34, in combination with increased suture management member deformability allows for greater surface area contact between the suture management member 60 and the legs 32 and 34.

In other configurations, instead of a portion of the suture management member 60 being received near the gap 40, a portion of the suture management member 60 can be received in the gap 40. Alternatively, while the suture management member 60 is illustrated as being received in one of the first enlarged opening 36 and the second enlarged opening 38, the suture management member 60 can be received in the other of the first enlarged opening 36 and the second enlarged opening 38, or be received in both the first enlarged opening 36 and the second enlarged opening 38. In the latter case, an intermediate portion of the suture management member 60 extends through the gap 40, such that the suture management member 60 has two enlarged ends and a narrower intermediate portion.

With continued reference to FIG. 2, a suture-receiving recess 74 is formed at one end of the suture management member 60. This recess 74 receives and selectively retains the end portions of a length of suture or suture length. For instance, following positioning a suture across an opening or arteriotomy, whether at the end of a procedure, or as part of a "pre-close" technique, the suture-receiving recess 74 can securely capture and hold the sutures until needed to close the opening or arteriotomy. The suture-receiving recess 74 extends from the upper surface 64 to the lower surface 66 and through transition end portion 68, while extending part-way through the suture management member 60 in a proximal to distal direction from the transition end portion 68 toward the transition end portion 70. Depending on the construction, the side walls of the suture-receiving recess 74 can be generally planar or curved and include surface features 76 that selectively engage and retain the suture disposed within the suture-receiving recess 74. Those surface features can include detents, barbs, tines, surface textures, whether uniform, unidirectional, or random, or other surface features.

Figure 27:
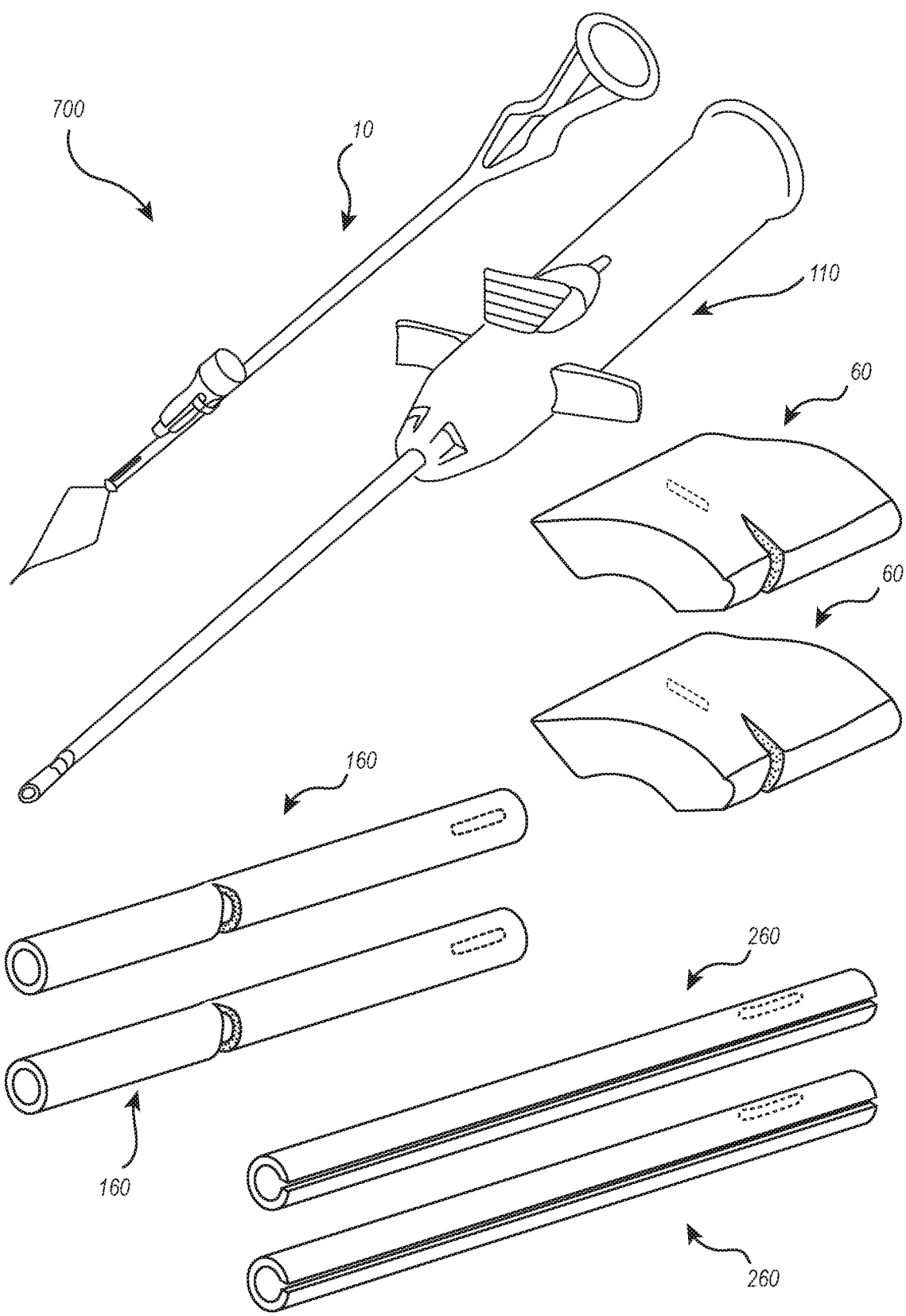
FIG. 27 schematically illustrates a kit according to an embodiment of the present invention.

Suture management member 60 is monolithic and can be constructed from a lubricous biocompatible polymer, such as polyethylene, high-density polyethylene, acrylonitrile butadiene styrene, polycarbonate, or other resiliently deformable materials. In addition, the suture management member 60 can include indicia 78 that provides information to the medical professional for use of multiple suture management members. For instance, the indicia 78 can be a letter, number, etc. and/or have a different color compared to a remainder of the suture management member 60. This color can be similar to a colored region R of the suture S so that the medical professional can associate similarly colored sutures and suture management members, thereby organizing the both sutures and suture management members. In addition, when multiple suture management members are included in a kit, such as the kit 700 illustrated in FIG. 27, with the suture handling device, such as a knot pusher or knot pusher/suture trimmer, and/or the devices used to position the sutures, each suture management member can be differently colored. For instance, the indicia for each suture management member can be different and/or the suture management members themselves can be differently colored to indicate a sequence of use so that a medical professional can identify which sutures are associated with which suture management member and so manipulate the suture management members, and associated sutures, in a particular order.

Figure 4:
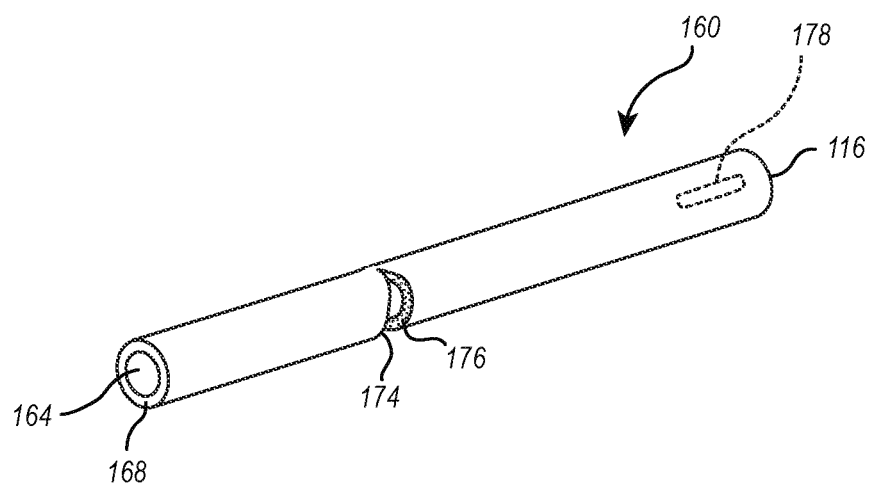
FIG. 4 illustrates a perspective view of another suture management member according to another configuration of the present invention.

Turning to FIG. 4, illustrated is an alternate suture management member 160. The discussion related to suture management member 60 is also applicable to suture management member 160, wherein like elements are referenced with like reference numerals. Further, the features, functions, and elements described in relation to suture management member 60, or other suture management member described herein, may be combinable with features, functions, and elements described in relation to suture management member 160, or any other embodiment depicted and/or described herein.

Figure 5:
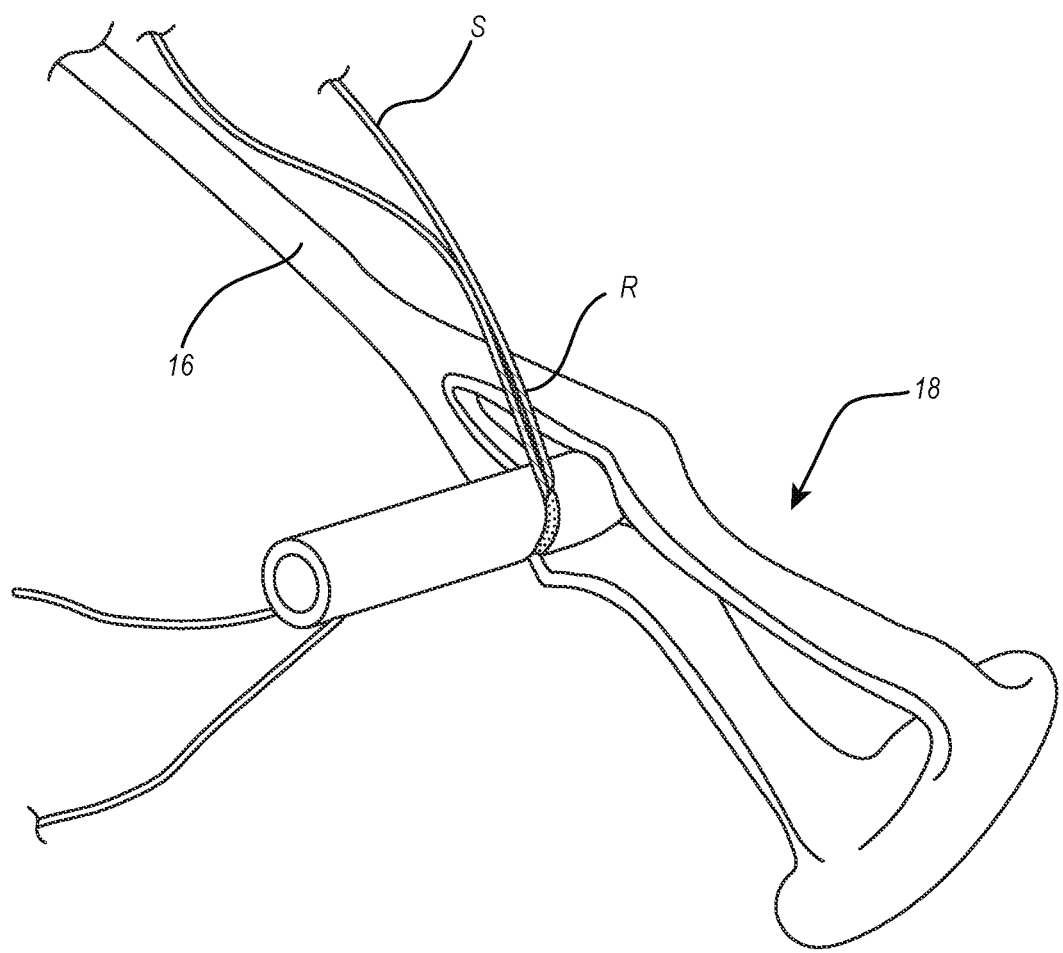
FIG. 5 illustrates a partial perspective view of the suture management member of FIG. 4 with the apparatus of FIG. 1.

As illustrated in FIGS. 4 and 5, suture management member 160 has an elongate body which includes an outer surface 162 that is generally profiled to cooperate with legs 32 and 34. In contrast to suture management member 60, suture management member 160 includes a lumen 164 extending in the extension direction from a proximal end 166 to a distal end 168 (while it is understood that one or more lumens can be included in any of the suture management members described herein or could be identified by one skilled in the art based upon this disclosure). The suture-receiving recess 174 extends transversely to a longitudinal axis of the suture management member 160. This recess 174 receives and selectively retains the end portions of a length of suture S or suture length S when the suture management member 160 is disposed within the opening 20 of the knot pusher, as illustrated in FIG. 5. The suture-receiving recess 174 extends part-way through a wall 170 extending between the outer surface 162 and the lumen 164, the remaining portion of the suture-receiving recess forming a living hinge. As shown, in FIG. 4, the suture-receiving recess 174 communicates with the lumen 164. However, the depth of the suture-receiving recess 174 can be less than the depth of the wall so that it does not communicate with the lumen 164 or the lumen 164 can be absent from the suture management member 160.

The profile of the body of suture management member 160 allows a portion of the suture management member 160 to be received in the opening 20 close to the gap 40, in one configuration. A similar effect can be achieved if the suture management member 160 is placed close to a distal end 46 of the second enlarged opening 38, or bifurcation of the legs 32 and 34 at the proximal end of the elongated member 16. Increasing the narrowness of the gap 40 or angular separation of the legs 32 and 34 at the bifurcation, can increase the pinching effect, when coupled with changing the resiliency or deformation characteristics of the suture management member 160. A narrower spacing between legs 32 and 34, in combination with increased suture management member deformability allows for greater surface area contact between the suture management member 160 and the legs 32 and 34.

In other configurations, instead of a portion of the suture management member 160 being received near the gap 40, a portion of the suture management member 160 can be received in the gap 40.

Depending on the construction, the side walls of the suture-receiving recess 174 can be generally planar or curved and include surface features 176 that selectively engage and retain the suture disposed within the suture-receiving recess 174. Those surface features can include detents, barbs, tines, surface textures, whether uniform, unidirectional, or random, or other surface features.

As with the suture management member 60, suture management member 160 can be constructed from a such as polyethylene, high-density polyethylene, acrylonitrile butadiene styrene, polycarbonate, or other resiliently deformable materials. In addition, the suture management member 160 can include indicia 178 that provides information to the medical professional for use of multiple suture management members. For instance, the indicia 178 can be similar to the indicia 78. As with suture management member 60, when multiple suture management members 160 are included in a kit, such as the kit 700 illustrated in FIG. 27, with the suture handling device, such as knot pusher or knot pusher/suture trimmer, and/or the devices used to position the sutures, each suture management member can be differently colored. For instance, the indicia for each suture management member can be different and/or the suture management members themselves can be differently colored to indicate a sequence of use so that a medical professional can identify which sutures are associated with which suture management member and so manipulate the suture management members, and associated sutures, in a particular order.

Figure 6A:
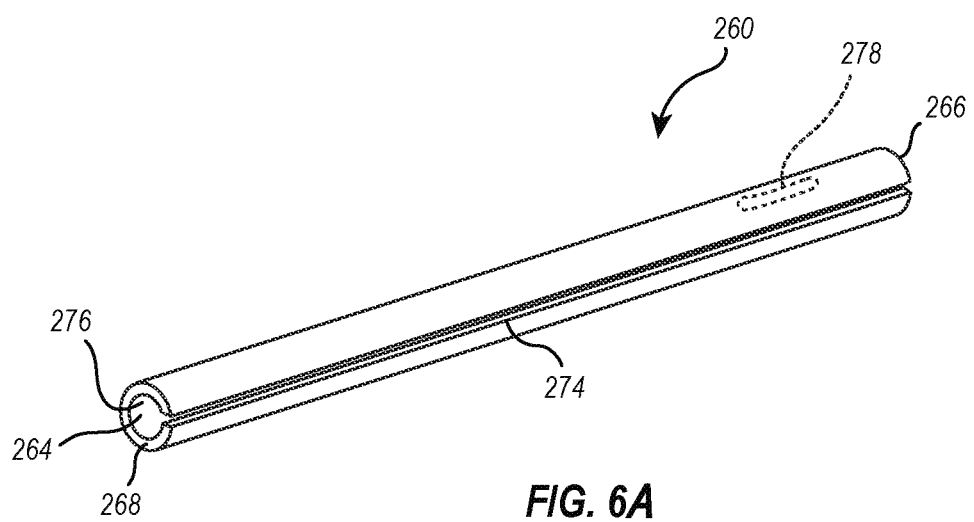
FIG. 6A illustrates a perspective view of another suture management member according to another configuration of the present invention.
Figure 6B:
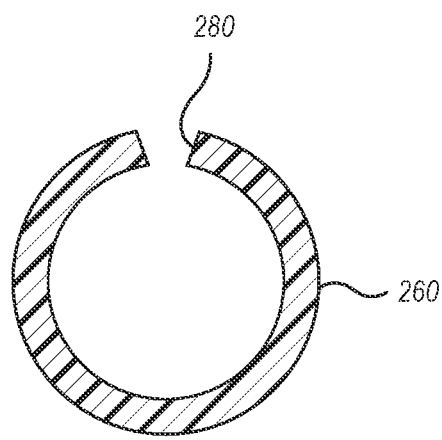
FIG. 6B illustrates a cross-sectional view of the another suture management member of FIG. 6A

Turning to FIGS. 6A-6B, illustrated is an alternate suture management member 160. The discussion related to suture management member 60 and suture management member 160 is also applicable to suture management member 260, wherein like elements are referenced with like reference numerals. Further, the features, functions, and elements described in relation to suture management member 60 and suture management member 160, or other suture management member described herein, may be combinable with features, functions, and elements described in relation to suture management member 260, or any other embodiment depicted and/or described herein.

Figure 7:
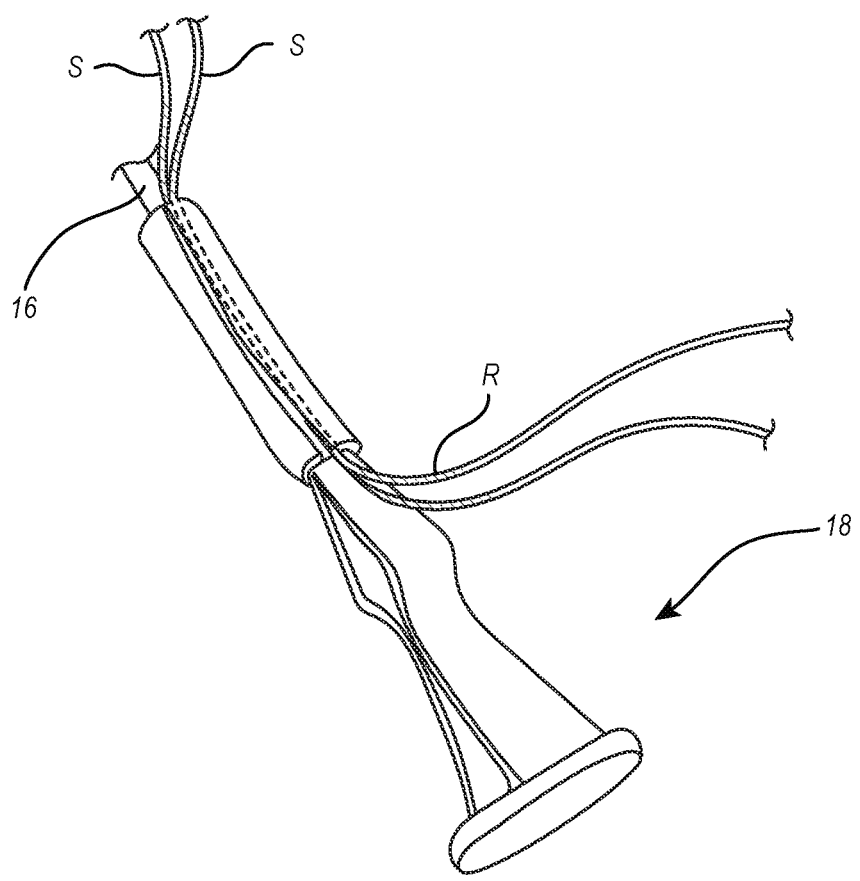
FIG. 7 illustrates a partial perspective view of the suture management member of FIG. 6A with the apparatus of FIG. 1.

As illustrated in FIGS. 6A-7, suture management member 260 has an elongate body which includes an outer surface 262 and a lumen 264 extending from a proximal end 266 to a distal end 268. The suture-receiving recess 274 extends through a wall 270 of the body, optionally with a chamfer 280, with the suture-receiving recess 274 communicating with the lumen 264. In contrast to suture management members 60 and 160, the suture management member 260 cooperates with the elongated member 16 of the knot pusher 20 to hold the lengths of suture or suture lengths. The lengths of suture S or suture lengths S pass through the suture-receiving recess 274 and are retained between the wall 270 and the elongated member 16, as illustrated in FIG. 7, when the elongated member 16 is received within the lumen 264. The suture-receiving recess 274 also functions as an expansion recess when the elongated member 16 is within the lumen 264. When the sutures are to be withdrawn, such as to close the opening or arteriotomy, they can be pulled directly through the suture-receiving recess 274 along the length of the body. This greater contact area between the wall 270 forming the lumen 264 and the outer surface of the elongated member 16 provides enhanced securing of the suture.

Depending on the construction, the lumen 264 of the suture-receiving recess 274 can be generally planar or curved and include surface features 276 that selectively engage and retain the suture disposed within the suture-receiving recess 274. Those surface features can include detents, barbs, tines, surface textures, whether uniform, unidirectional, or random, or other surface features.

Figure 8:
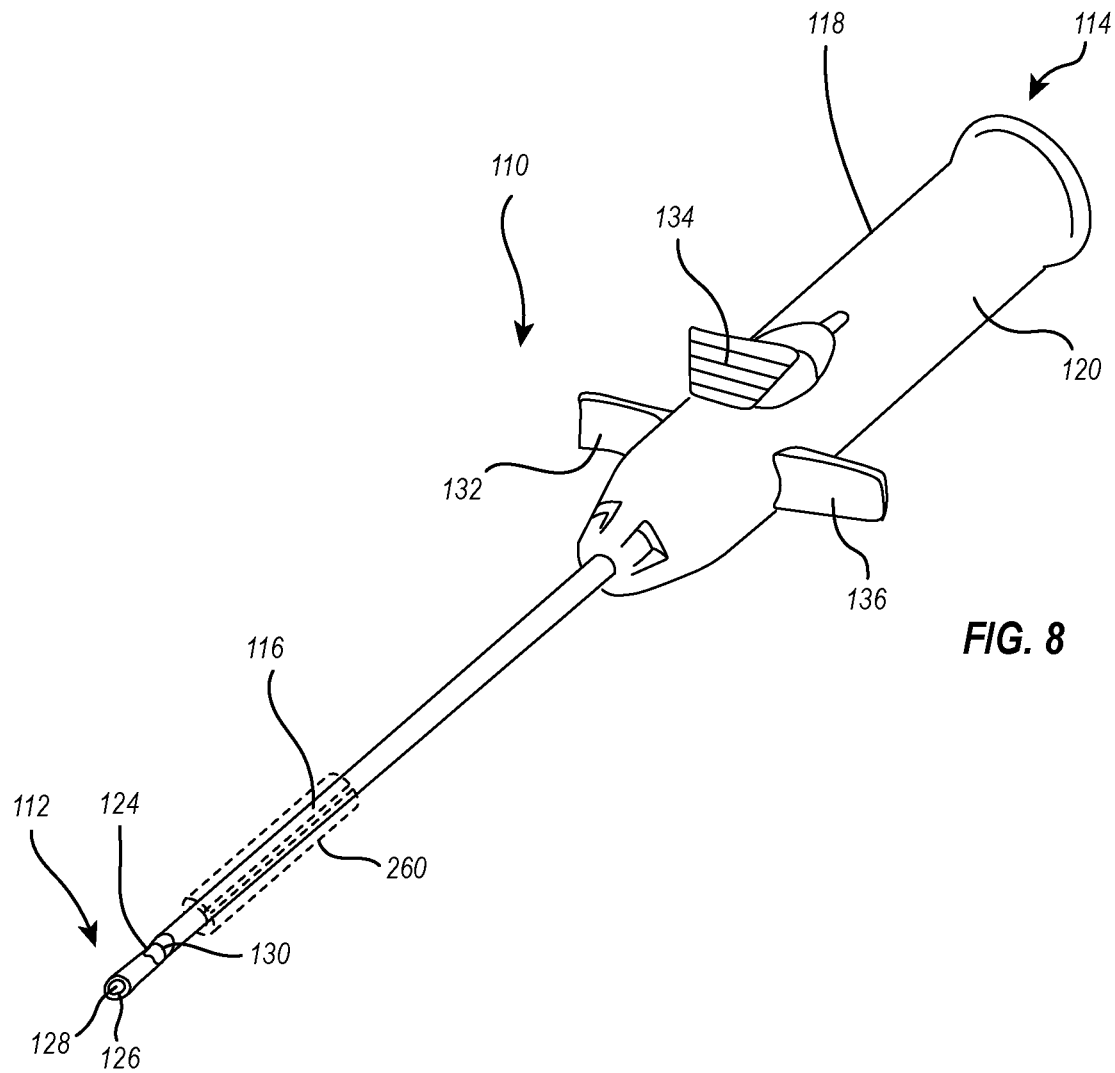
FIG. 8 illustrates a perspective view of an alternate embodiment of an apparatus used to advance a surgical knot along a suture length.

As with the suture management members 60 and 260, suture management member 260 can be constructed from a such as polyethylene, high-density polyethylene, acrylonitrile butadiene styrene, polycarbonate, or other resiliently deformable materials. In addition, the suture management member 160 can include indicia 278 that provides information to the medical professional for use of multiple suture management members. For instance, the indicia 278 can be similar to the indicia 78. As with suture management member 60, when multiple suture management members 260 are included in a kit, such as the kit 700 illustrated in FIG. 27, with the suture handling device, such as a knot pusher or knot pusher/suture trimmer, and/or the devices used to position the sutures, each suture management member can be differently colored. For instance, the indicia for each suture management member can be different and/or the suture management members themselves can be differently colored to indicate a sequence of use so that a medical professional can identify which sutures are associated with which suture management member and so manipulate the suture management members, and associated sutures, in a particular order An alternate apparatus used to advance a surgical knot along a suture length is illustrated in FIG. 8. Each of the suture management members described herein could be used with the knot pusher/suture trimmer 110 of FIG. 8. For instance, as illustrated in phantom lines, the suture management member 260 is mounted to a portion of the knot pusher/suture trimmer 110. The knot pusher/suture trimmer 110, as an example of a suture handling device, while similar to the knot pusher 10 in many respects, further includes a cutting member 130 that allows the knot pusher/suture trimmer 110 to not only advance the surgical knot along the suture length, but also trim the suture following tightening of knot in place against tissue. Like features or structure between the knot pusher 10 and the knot pusher/suture trimmer 110 are identified with like reference numerals. Further the description relates to the knot pusher 10 is also applicable to that of the knot pusher/suture trimmer 110, and vice versa.

The knot pusher/suture trimmer 110, therefore, includes a distal end 112 and a proximal end 114. Proximally extending from the distal end 112 is an elongated member 116, which extends to a handle portion 118. As shown, the suture management member 260 can mount to the elongated member 116. Unlike the handle 18 of knot pusher 10, the handle 118 includes a handle body 122 from which extends a lever 132 that is coupled to a proximal end of the cutting member 130. Also extending from the handle body 122 is a lever 134 and a support 136. Manipulating the lever 134 advances a suture retainer (not shown) distally to capture the suture within the proximal slot 126 and the lumen 128 that terminates at the aperture 126. The support 136 provides a location for the medical professional to grasp during movement of the levers 132 and 134. Additional details of the knot pusher/suture trimmer 110 can be found in U.S. Pat. No. 7,992,571, which are incorporated herein in their entireties by this reference.

As mentioned before, when the sutures are managed by the suture management members, such as following a "pre-close" technique, it is desirable to position the end portions of the suture, and optionally the knot pushers, for subsequent use without impeding access to the surgical site. One way to so position the sutures is through a support assembly that selectively cooperates with the surgical drapes or to some other structure within access to the medical professional.

Figure 9:
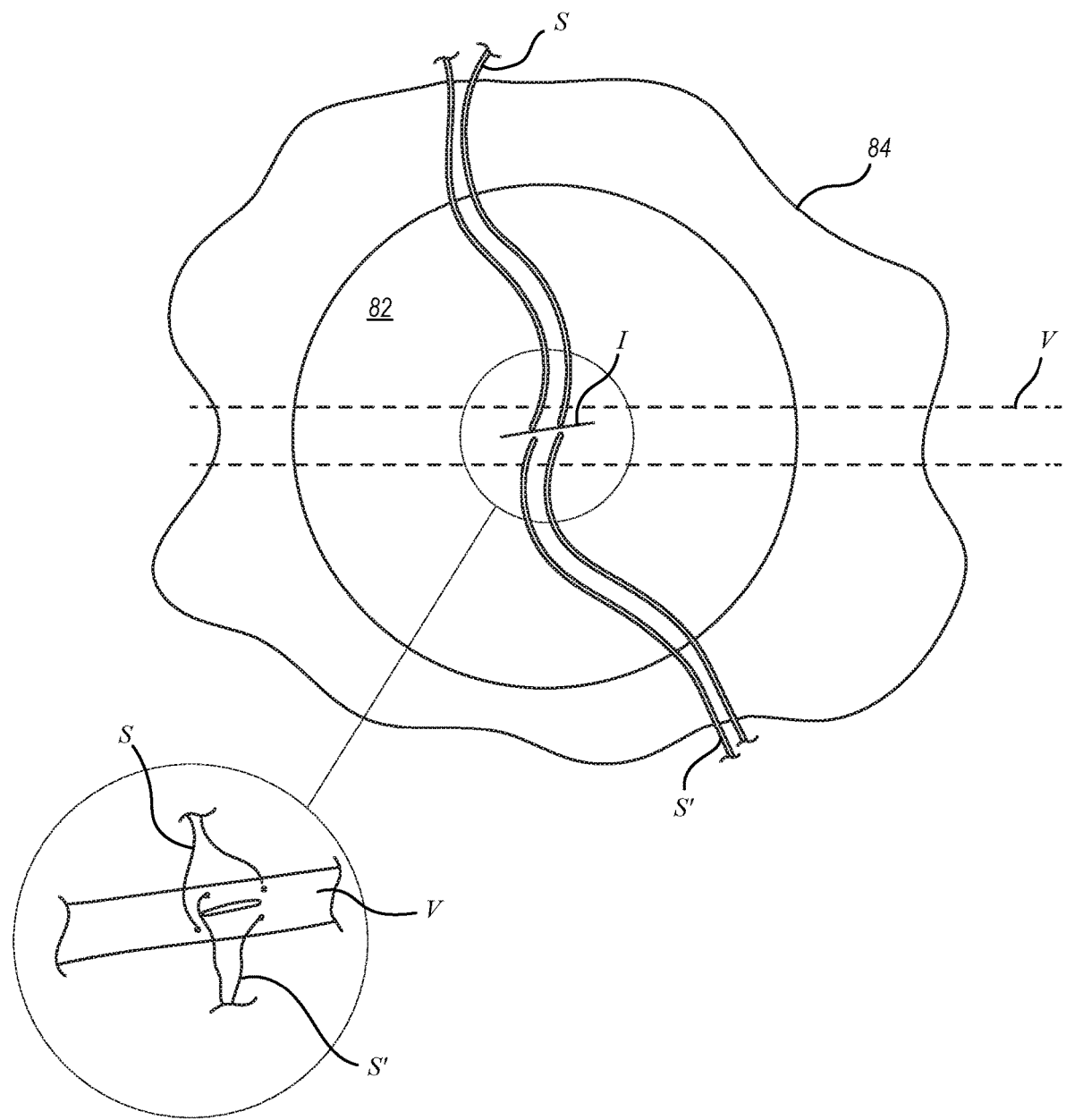
FIG. 9 illustrates a top view of a surgical site that can be accessed and closed using the apparatus of the present invention.

As illustrated in FIG. 9, a surgical site 80 of a patient 82 is surrounded by a surgical drape 84 that isolates the surgical site 80 from a remainder of the patient 82 and prevents unwanted contamination. FIG. 9 illustrates a situation where two suture loops, S and S', have been previously positioned through a wall of a vessel V, such as using a "pre-close" technique. The end portions of the suture loops S and S' extend through an incision I and are to be secured through the suture management members described herein.

Figure 10:
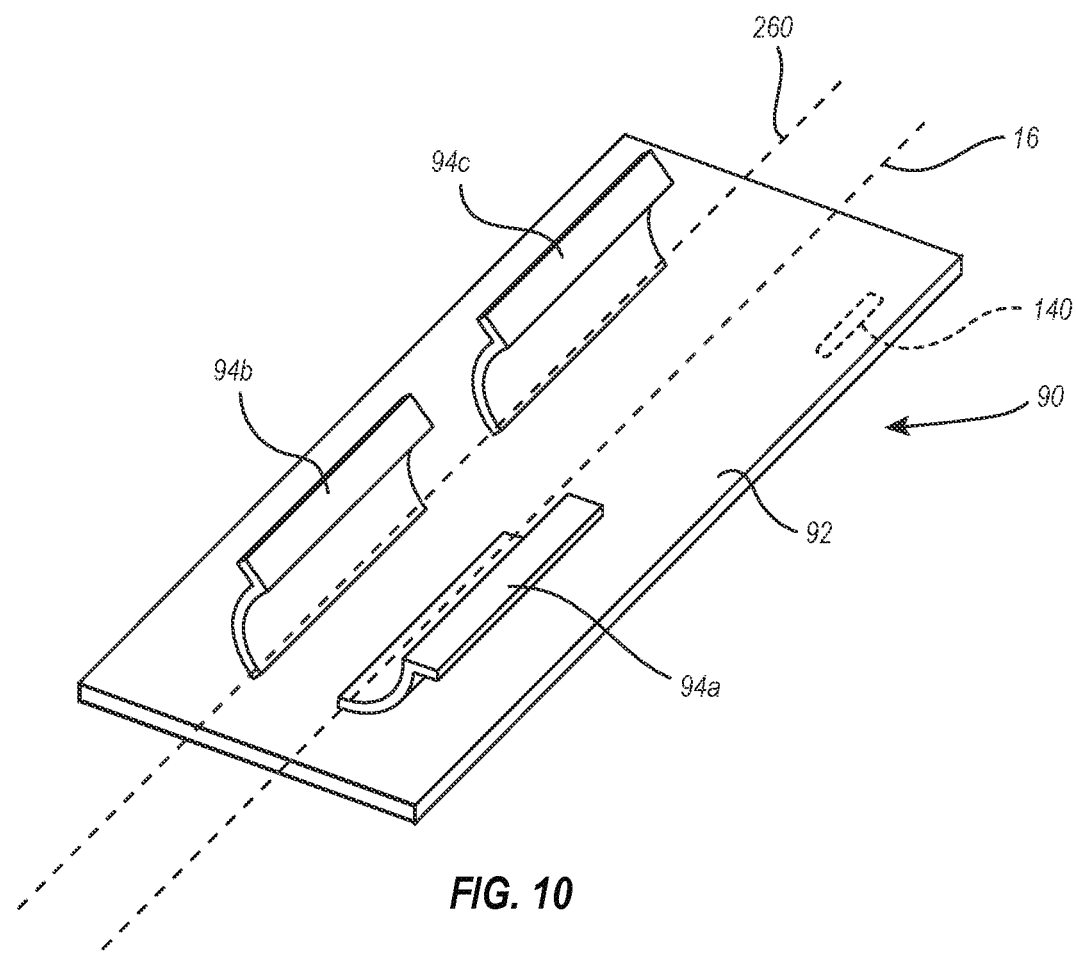
FIG. 10 is a perspective view of a support assembly according to an embodiment of the present invention.
Figure 11:
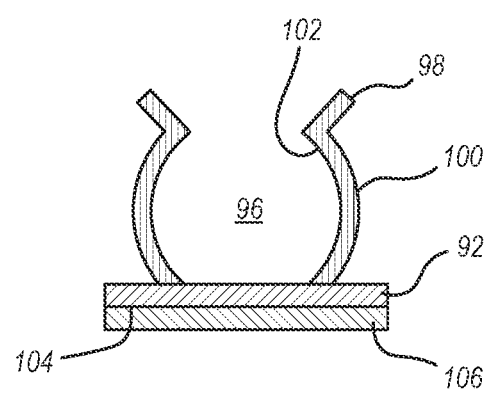
FIG. 11 is a cross-sectional side view of the support assembly of FIG. 10 according to an embodiment of the present invention.

Turning to FIGS. 10 and 11, illustrated is a support assembly 90 that can support both the knot pusher 10 and the suture management member 260, for example, and help to secure the suture loops relative to an incision or a surgical site. While the following discussion is made relative to the suture management member 260, a similar discussion can be provided for the other suture management members described herein in cooperation with the support assemblies.

The support assembly 90 supports the elongated member 16 of the knot pusher 10, and optionally directly supports and contacts the suture management member 260. The support assembly 90 selectively attaches to a surgical drape, such as surgical drape 84, and is used to hold the knot pusher 10 and suture management member until the medical professional needs to access the sutures to close the opening or arteriotomy. The support assembly 90 includes portion(s) securing the knot pusher, and/or suture management member, while also including portion(s) attaching or coupling with the surgical drape or other structure accessible to the medical professional and that could support the support assembly 90, such as tables, trays, or other supports.

As illustrated in FIGS. 10 and 11, a support assembly 90 according to one configuration includes a base 92, such as a mounting portion, from which extends arms 94, such as a securing portion. The base 92 couples to a support, such as the surgical drape 84, through a coupling structure 106 mounted to a lower surface 104. For instance, the coupling structure 106 can be an adhesive strip on the bottom of the base 92. The adhesive strip can include a peel-away portion that can be removed to expose the adhesive for bonding or coupling to the support Alternatively, the coupling structure 106 can include hook and loop fasteners, complementary detents, clips, studs, pins, etc.

The arms 94 form a channel 96 extending longitudinally along the base 92. Two of the arms 94a, b are spaced apart from each other and a third arm 94c is longitudinally spaced from arms 94a, b. With the suture management member having a cross-sectional dimension larger than a cross-sectional dimension of the knot pusher 10, support assembly 90 can accommodate the cross-sectional dimension difference. The two arms 94a, b hold the knot pusher 10, while the third arm 94c rests against the suture management member.

The arms 94 are resiliently deformable to accommodate the elongated member 16 of the knot pusher 10, and/or the suture management member, within the channel 96. As the elongated member 16 is moved toward the base 92, it engages outwardly extending wings 98 of the arms 94; each wing 98 being at an end of a curved portion 100. The downward force pushes the wings 98 outwardly and allows the knot pusher 10 to move into the channel 96 formed by the curved portions 100. When received in the channel 96, the resilience of the arms 94 returns the arms 94 toward their unmoved, pre-engagement position so the curved portions 100 surround a curved outer surface of the elongated member 16. With a curved surface 102 of the curved portions approximating the outer surface of the elongated member 16, the support assembly 90 securely retains the knot pusher 10.

While the support assembly 90 illustrated in FIGS. 10 and 11 includes three arms 94a, b, c, and reference is made to the third arm 94c contacting the suture management member and the two arms 94a, b contacting the knot pusher 10, alternate configurations can hold the knot pusher 10 and the suture management member in different ways. For instance, the two arms 94a, b hold the suture management member, with the knot pusher 10 extending through its lumen, and the third arm 94c supports the knot pusher 10. In still another configuration, all three arms 94a, b, c contact the suture management member. In still other configurations, more or less arms extend from the base 92 rather than just 3 arms, as illustrated. For instance, the number of arms can range from about 2 to about 7.

The support assembly 90 can be constructed from a variety of materials. For instance, the base and arms can be constructed from a polymer, stainless steel, or other materials or combinations thereof, so long as the material provides (i) the base with a desired rigidity or flexibility based upon the support to which is attached by the coupling structure 106 and (ii) the arms with the desired rigidity or flexibility to receive and accommodate the elongated member and/or the suture management member as described herein. It will be understood, that the materials forming the base and arms need not be the same, but can be if the identified functions can be achieved through the material, configuration of the base and/or arm, or through a combination of both function and configuration. It is also possible to utilize a material having desired lubricity to aid with position of a device between the arms.

In addition, the base 92, or more generally, the support assembly 90 can include indicia 140 that provides information to the medical professional for use of multiple suture management members. For instance, the indicia 140 can be a letter, number, etc. and/or have a different color compared to a remainder of the base 92 or support assembly 90. This color can be similar to a colored region R of the suture S, the color of the suture management member, and/or the color of the indicia associated with the suture management member so that the medical professional can associate similarly colored sutures, suture management members, and/or support assemblies, thereby organizing the sutures, suture management members, and support assemblies. In addition, when multiple suture assemblies are included in a kit, such as the kit 700 illustrated in FIG. 27, with the suture handling device, such as a knot pusher or knot pusher/suture trimmer, the suture management member, and/or the devices used to position the sutures, each support assembly can be differently colored. For instance, the indicia for each support assembly can be different and/or the suture management members themselves can be differently colored to indicate a sequence of use so that a medical professional can identify which sutures are associated with which suture management member and so manipulate the support assembly, the suture management members, and associated sutures, in a particular order.

Figure 12:
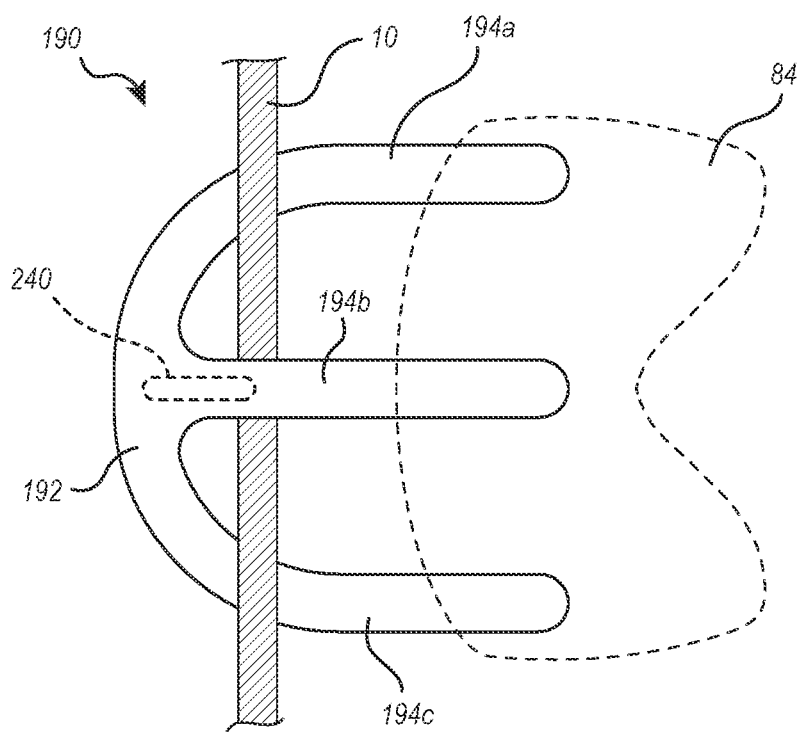
FIG. 12 is a top view of another support assembly according to an embodiment of the present invention.
Figure 13:
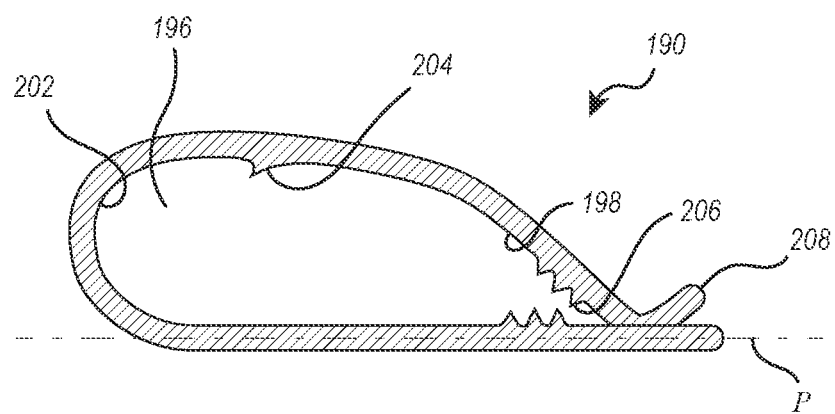
FIG. 13 is a cross-sectional side view of the support assembly of FIG. 12 according to an embodiment of the present invention.

Turning to FIGS. 12-13 illustrated is an alternate configuration of a support assembly that can support a knot pusher and a suture management member and aid with securing the suture loops relative to an incision or a surgical site. The discussion related to the support assembly 90 is also applicable to the support assembly 190, wherein like elements are referenced with like reference numerals. Further, the features, functions, and elements described in relation to each of the support assemblies may be combinable with features, functions, and elements described in relation to any other the support assembly.

As illustrated in FIGS. 12 and 13, a support assembly 190 according to one configuration includes a base 192, such as a mounting portion, from which extends arms 194, such as securing portions. The arms 194 both capture the elongated member 16 of the knot pusher 10, and couple to a support, such as the surgical drape 84. The arms 194 are arranged in a trident like orientation, with two arms 194a and 194c lying generally in the same plane P, while the arm 194b extends from the base 192 and curves away and then toward the plane P. The arm 194b can traverse the plane P or have an end 208 spaced from the plane P. The arms 194a, b, c and in operative relationship to capture the surgical drape 84, which provides a fixing point for the support assembly 190. For instance, the arm 194b can be resiliently deformable so that when deformed by capturing the surgical drape 84, a force towards the plane P holds the surgical drape 84 between the arm 194b and arms 194a and 194c. Alternatively, one or more of the arms 194a, b, c can be biased toward each other in a direction transverse to the plane P; the biasing force from the arms 194a, b, c holding the surgical drape 84.

One or more of the arms 194a, b, c can optionally include a coupling structure 106 to aid with retaining the surgical drape 84. The coupling structure 206 can be an adhesive strip on a lower surface 198 of the arm 194b and/or an upper surface 200 of arms 194a, 194b. The adhesive strip can include a peel-away portion that can be removed to expose the adhesive for bonding or coupling to the support. Alternatively, the coupling structure 106 can include hook and loop fasteners, complementary detents, teeth, clips, studs, pins, etc.

The arms 194a, b, c form a channel 196 that extends beside the base 192 transversely to an extension direction of the arms 194a, b, c. With the elongated member 16 in the channel 196, a portion rests on the upper surface 200 of the arms 194a, b, while a portion rests on the lower surface 198 of arms 194b. With the arms 194a, b, c being resiliently deformable, the downward force of the arm 194b and the upward force of the arms 194a and 194b as they each move towards the pre-engagement position hold the elongated member 16 of the knot pusher 10, and/or the suture management member, within the channel 196. In the engagement position, the lower surface 198 surrounds a curved outer surface of the elongated member 16. With a curved surface 202 of the curved portions approximating the outer surface of the elongated member 16, the support assembly 190 securely retains the knot pusher 10.

A retaining member 204 extends from the lower surface 198 near the channel 196 and prevents movement of the elongated member 16 towards the end 208 of the arm 194b. The retaining member 204, as illustrated, curves away from the lower surface 198 and then towards the channel 196 and base 192. However, the retaining member 204 can curve in other directions, such as away from the channel 196 and base 192 or can extend in a direction perpendicular to the lower surface 198.

While the support assembly 190 illustrated in FIGS. 12 and 13 include three arms 194a, b, c, it will be understood that a greater number of arms could also be used. Furthermore, while FIGS. 12 and 13 illustrate the elongated member 16 disposed within the channel 196, in alternate configurations, a portion of the suture management member can be received in the channel 196. In still other configurations, the suture management member can cooperate and reference is made to the third arm 94c contacting the suture management member and the two arms 94a, b contacting the knot pusher 10, alternate configurations can cooperate with or contact one of the two arms 194a and 194c, while the elongated member 16 is in operative relationship with the arm 194b within the channel 196.

The support assembly 190 can be constructed from a variety of materials. For instance, the base and arms can be constructed from a polymer, stainless steel, or other materials or combinations thereof, so long as the material provides (i) the support assembly with a desired rigidity or flexibility to capture and hold a portion of the knot pusher and/or the suture management member. It will be understood, that the materials forming the base and arms need not be the same, but can be if the identified functions can be achieved through the material, configuration of the base and/or arm, or through a combination of both function and configuration.

In addition, the base 192, or more generally, the support assembly 190 can include indicia 240 that provides information to the medical professional for use of multiple suture management members. For instance, the indicia 240 can be a letter, number, etc. and/or have a different color compared to a remainder of the base 192 or support assembly 190. This color can be similar to a colored region R of the suture S, the color of the suture management member, and/or the color of the indicia associated with the suture management member so that the medical professional can associate similarly colored sutures, suture management members, and/or support assemblies, thereby organizing the sutures, suture management members, and support assemblies. In addition, when multiple suture assemblies are included in a kit, such as the kit 700 illustrated in FIG. 27, with the suture handling device, such as knot pusher or knot pusher/suture trimmer, the suture management member, and/or the devices used to position the sutures, each support assembly can be differently colored. For instance, the indicia for each support assembly can be different and/or the suture management members themselves can be differently colored to indicate a sequence of use so that a medical professional can identify which sutures are associated with which suture management member and so manipulate the support assembly, the suture management members, and associated sutures, in a particular order.

Figure 14:
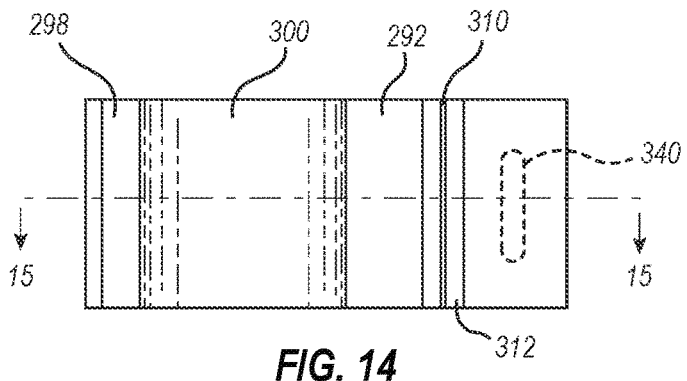
FIG. 14 is a top view of another support assembly according to an embodiment of the present invention.
Figure 15:
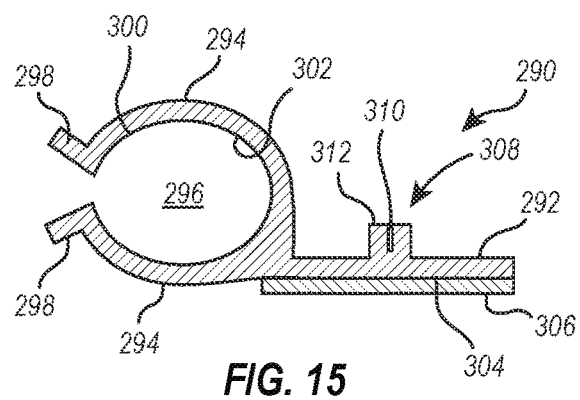
FIG. 15 is a cross-sectional side view of the support assembly of FIG. 14 according to an embodiment of the present invention.

Turning to FIGS. 14-15, illustrated is an alternate configuration of a support assembly that can support a knot pusher and a suture management member and aid with securing the suture loops relative to an incision or a surgical site. The discussion related to the support assemblies 90 and 190 are also applicable to the support assembly 290, wherein like elements are referenced with like reference numerals. Further, the features, functions, and elements described in relation to each of the support assemblies may be combinable with features, functions, and elements described in relation to any other the support assembly.

As illustrated in FIG. 14, a support assembly 290 according to one configuration includes a base 292, such as a mounting portion, from which extends arms 294, such as securing portions. The base 292 couples to a support, such as the surgical drape 84 (FIG. 9), through a coupling structure 306 mounted to a lower surface 304. For instance, the coupling structure 306 can be an adhesive strip on the bottom of the base 292. The adhesive strip can include a peel-away portion that can be removed to expose the adhesive for bonding or coupling to the support. Alternatively, the coupling structure 106 can include hook and loop fasteners, complementary detents, clips, studs, pins, etc.

Extending from the base 292 is a suture retainer 308 having a groove or slit 310 between two wall portions 312. The groove 310 is configured to receive lengths of suture supported or secured by the suture management member. In this configuration, the slit 310 extends in the same direction as a channel 296 formed by two arms 294. In other configurations, the slit 310 can be transverse to a longitudinal axis of the channel 296.

The arms 294 that form the channel 296 extend transversely to an extension direction of the base 292, or a direction in which the base 292 is elongate. The arms 294 *a, b* are spaced apart from each. The arms 294 are resiliently deformable to accommodate the elongated member 16 of the knot pusher 10, and/or the suture management member, within the channel 296. As the elongated member 16 is moved toward the base 292, it engages outwardly extending wings 298 of the arms 294; each wing 298 being at an end of a curved portion 300. The wings 298 are moved outwardly as the knot pusher 10, and/or the suture management member, is moved toward the channel 296. When received in the channel 296, the resilience of the arms 294 returns the arms 294 toward their unmoved, pre-engagement position so the curved portions 300 surround a curved outer surface of the elongated member 16. With a curved surface 302 of the curved portions approximating the outer surface of the elongated member 16, the support assembly 290 securely retains the knot pusher 10.

As discussed previously, the arms 294*a, b* can hold the elongated member of the knot pusher, the suture management member, or both the knot pusher and the suture management member. In still other configurations, more arms extend from the base 292 rather than just 2 arms, as illustrated. For instance, longitudinally spaced pairs of arms can extend from the base 292.

The support assembly 290 can be constructed from a variety of materials. For instance, the base and arms can be constructed from a polymer, stainless steel, or other materials or combinations thereof, so long as the material provides (i) the base with a desired rigidity or flexibility based upon the support to which is attached by the coupling structure 306 and (ii) the arms with the desired rigidity or flexibility to receive and accommodate the elongated member and/or the suture management member as described herein. It will be understood, that the materials forming the base and arms need not be the same, but can be if the identified functions can be achieved through the material, configuration of the base and/or arm, or through a combination of both function and configuration.

In addition, the base 292, or more generally, the support assembly 290 can include indicia 340 that provides information to the medical professional for use of multiple suture management members. For instance, the indicia 340 can be a letter, number, etc. and/or have a different color compared to a remainder of the base 292 or support assembly 290. This color can be similar to a colored region R of the suture S, the color of the suture management member, and/or the color of the indicia associated with the suture management member so that the medical professional can associate similarly colored sutures, suture management members, and/or support assemblies, thereby organizing the sutures, suture management members, and support assemblies. In addition, when multiple suture assemblies are included in a kit, such as the kit 700 illustrated in FIG. 27, with the suture handling device, such as a knot pusher or knot pusher/suture trimmer, the suture management member, and/or the devices used to position the sutures, each support assembly can be differently colored. For instance, the indicia for each support assembly can be different and/or the suture management members themselves can be differently colored to indicate a sequence of use so that a medical professional can identify which sutures are associated with which suture management member and so manipulate the support assembly, the suture management members, and associated sutures, in a particular order.

Figure 16:
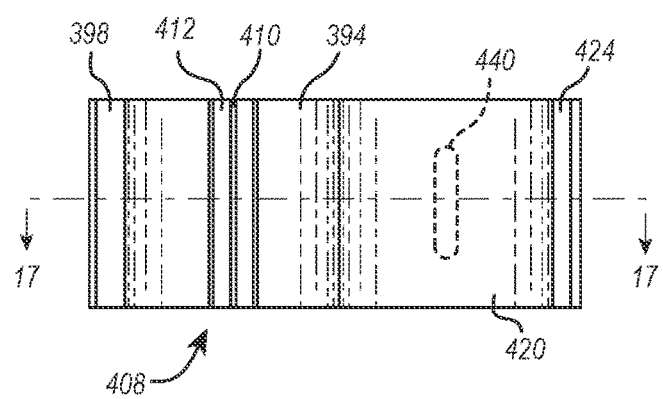
FIG. 16 is a top view of another support assembly according to an embodiment of the present invention.
Figure 17:
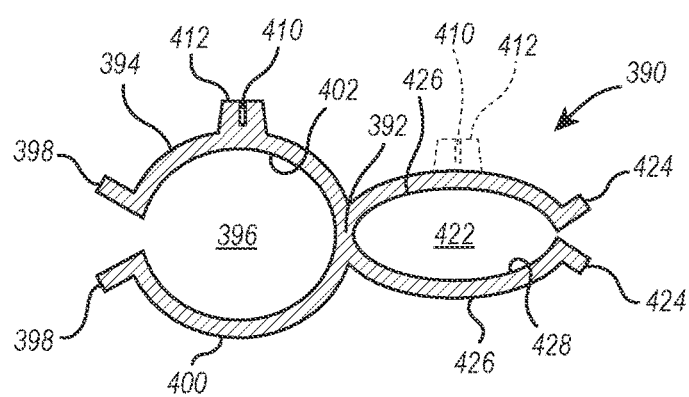
FIG. 17 is a cross-sectional side view of the support assembly of FIG. 16 according to an embodiment of the present invention.

Turning to FIGS. 16-17, illustrated is an alternate configuration of a support assembly that can support a knot pusher and a suture management member and aid with securing the suture loops relative to an incision or a surgical site. The discussion related to the support assembly 90, 190, and 290 are also applicable to the support assembly 390, wherein like elements are referenced with like reference numerals. Further, the features, functions, and elements described in relation to each of the support assemblies may be combinable with features, functions, and elements described in relation to any other the support assembly.

As illustrated in FIGS. 16-17, a support assembly 390 according to one configuration includes a base portion 392, such as a mounting portion, from which extends two different sets of arms; arms 394 and arms 420, such as securing portions. The arms 394 form a channel 396 that receives a portion of a knot pusher and/or the suture management member. The arms 394 are resiliently deformable to accommodate the elongated member 16 of the knot pusher 10, and/or the suture management member, within the channel 396. As the elongated member 16 is moved toward the base 392, it engages outwardly extending wings 398 of the arms 394; each wing 398 being at an end of a curved portion 400. The wings 398 are moved outwardly as the knot pusher 10, and/or the suture management member, is moved toward the channel 396. When received in the channel 396, the resilience of the arms 394 returns the arms 394 toward their unmoved, pre-engagement position so the curved portions 400 surround a curved outer surface of the elongated member 16. With a curved surface 402 of the curved portions approximating the outer surface of the elongated member 16, the support assembly 390 securely retains the knot pusher 10.

Extending from one of the arms 394 is a suture retainer 408 having a groove or slit 410 between two wall portions 412. The groove 410 is configured to receive lengths of suture supported or secured by the suture management member. In this configuration, the slit 410 extends in the same direction as a channel 396 formed by two arms 394. In other configurations, the slit 410 can be transverse to a longitudinal axis of the channel 396. In still other configurations, the suture retainer 408 or another suture retainer 408 can be located on one of the arms 410, as illustrated in phantom in FIG. 16.

The arms 420 are similar to the arms 394, however they receive the support, such as the surgical drape 84 (FIG. 9). For instance, the arms 420 are resiliently deformable to accommodate the surgical drape 84 within a channel 422. As the surgical drape 84 is moved toward the base portion 392, it engages outwardly extending wings 424 of the arms 420; each wing 422 being at an end of a curved portion 424. The wings 422 are moved outwardly as the surgical drape 84 (FIG. 9), is moved toward the channel 422. When received in the channel 422, the resilience of the arms 420 returns the arms 420 toward their unmoved, pre-engagement position and pinch the surgical drape 84. The arms 420 can various shapes and configurations to aid with capturing and holding the surgical drape 84. For instance, the tension applied only by the arms themselves can be sufficient to hold the surgical drape. Alternatively, a portion of a curved surface 428 of a curved portion 426, and/or a portion of the wings 424, can include teeth, detents, textured surface finishes, that increase the frictional engagement or mechanically-operatively secure the surgical drape 84.

While the support assembly 390 illustrated in FIGS. 16-17 includes two sets of arms, the support assembly 390 can include a greater number of arm sets. For instance, additional pairs of arms 394 and/or arms 420 can be included in a side-by-side relationship along a longitudinal axis of the channel 396 or channel 422.

The support assembly 390 can be constructed from a variety of materials. For instance, the base and arms can be constructed from a polymer, stainless steel, or other materials or combinations thereof, so long as the material provides the desired rigidity or flexibility to operate as described herein. It will be understood, that the materials forming the base portion and arms need not be the same, but can be if the identified functions can be achieved through the material, configuration of the base portion and/or arm, or through a combination of both function and configuration.

In addition, the base 392, or more generally, the support assembly 390 can include indicia 440 that provides information to the medical professional for use of multiple suture management members. For instance, the indicia 440 can be a letter, number, etc. and/or have a different color compared to a remainder of the base 392 or support assembly 390. This color can be similar to a colored region R of the suture S, the color of the suture management member, and/or the color of the indicia associated with the suture management member so that the medical professional can associate similarly colored sutures, suture management members, and/or support assemblies, thereby organizing the sutures, suture management members, and support assemblies. In addition, when multiple suture assemblies are included in a kit, such as the kit 700 illustrated in FIG. 27, with the suture handling device, such as a knot pusher or knot pusher/suture trimmer, the suture management member, and/or the devices used to position the sutures, each support assembly can be differently colored. For instance, the indicia for each support assembly can be different and/or the suture management members themselves can be differently colored to indicate a sequence of use so that a medical professional can identify which sutures are associated with which suture management member and so manipulate the support assembly, the suture management members, and associated sutures, in a particular order.

Figure 18:
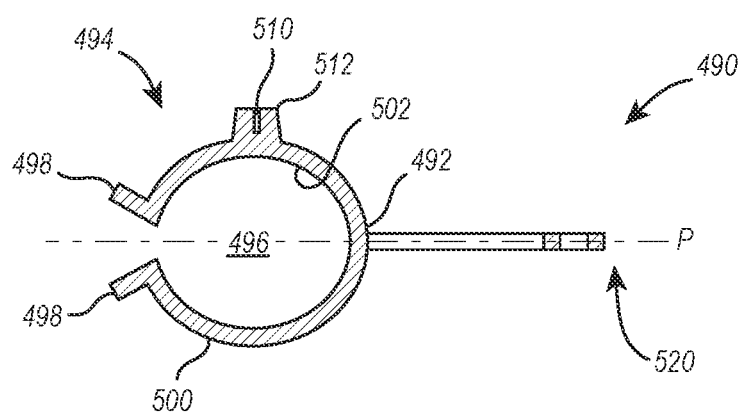
FIG. 18 is a perspective view of another support assembly according to an embodiment of the present invention.
Figure 19:
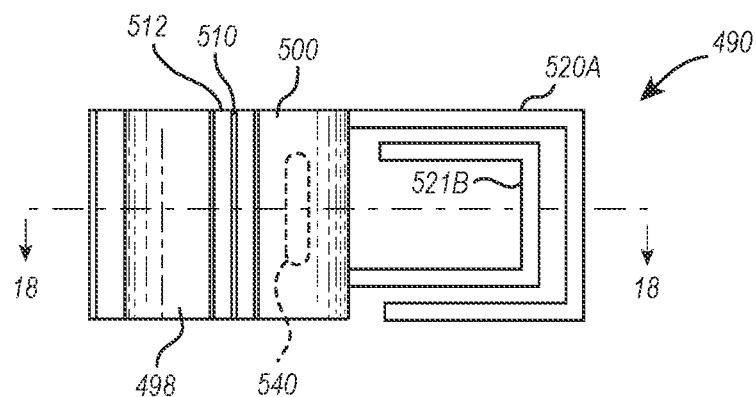
FIG. 19 is a cross-sectional side view of the support assembly of FIG. 18 according to an embodiment of the present invention.

Turning to FIGS. 18-19, illustrated is an alternate configuration of a support assembly that can support a knot pusher and a suture management member and aid with securing the suture loops relative to an incision or a surgical site. The discussion related to the support assembly 90, 190, 290, and 390 are also applicable to the support assembly 490, wherein like elements are referenced with like reference numerals. Further, the features, functions, and elements described in relation to each of the support assemblies may be combinable with features, functions, and elements described in relation to any other the support assembly.

As illustrated in FIGS. 18-19, a support assembly 490 according to one configuration includes a base portion 492, such as a mounting portion, from which extends two different sets of arms; arms 494 and arms 520, such as securing portions. The arms 494 form a channel 496 that receives a portion of a knot pusher and/or the suture management member. The arms 494 are resiliently deformable to accommodate the elongated member 16 of the knot pusher 10, and/or the suture management member, within the channel 496. As the elongated member 16 is moved toward the base 492, it engages outwardly extending wings 498 of the arms 494; each wing 498 being at an end of a curved portion 500. The wings 498 are moved outwardly as the knot pusher 10, and/or the suture management member, is moved toward the channel 496. When received in the channel 496, the resilience of the arms 494 returns the arms 494 toward their unmoved, pre-engagement position so the curved portions 500 surround a curved outer surface of the elongated member 16. With a curved surface 502 of the curved portions approximating the outer surface of the elongated member 16, the support assembly 490 securely retains the knot pusher 10.

Extending from one of the arms 494 is a suture retainer 508 having a groove or slit 510 between two wall portions 512. The groove 510 is configured to receive lengths of suture supported or secured by the suture management member. In this configuration, the slit 510 extends in the same direction as a channel 496 formed by two arms 494. In other configurations, the slit 510 can be transverse to a longitudinal axis of the channel 496.

The arms 520a and 520b receive the support, such as the surgical drape 84 (FIG. 9). The arms 520a and 520b are resiliently deformable to accommodate the surgical drape 84 therebetween, with the arms 520a and 520b moving relative to one another. The arms 520a and 520b are looped, with both extending from the base 492, but looping in opposite directions. While generally lying in the same plane P in a pre-engagement orientation, with the surgical drape 84 between the arms 520a and 520b, the resiliency of the arms 520a and 520b, or torsion and elasticity of the arms 520a and 520b, holds the surgical drape 84, as the arms 520a and 520b attempt to move towards the plane P. The arms 520a and 520b can various shapes and configurations to aid with capturing and holding the surgical drape 84. For instance, one of the arms can be more resilient and less likely to move, with the other arm moving to accommodate to the surgical drape. Stated another way, one arm can be fixed while the other arm is movable relative to the fixed arm. Either of the arms 520a and 520b can be the fixed arm or the movable arm. A portion of the arms 520a and 520b, such as the surfaces opposing one another, can include teeth, detents, textured surface finishes, that increase the frictional engagement or mechanically-operatively secure the surgical drape 84.

While the support assembly 590 illustrated in FIGS. 18-19 includes two sets of arms, the support assembly 490 can include a greater number of arm sets. For instance, additional pairs of arms 494 and/or arms 520 can be included.

The support assembly 490 can be constructed from a variety of materials. For instance, the base and arms can be constructed from a polymer, stainless steel, or other materials or combinations thereof, so long as the material provides the desired rigidity or flexibility to operate as described herein. It will be understood, that the materials forming the base portion and arms need not be the same, but can be if the identified functions can be achieved through the material, configuration of the base portion and/or arm, or through a combination of both function and configuration.

In addition, the base 492, or more generally, the support assembly 490 can include indicia 540 that provides information to the medical professional for use of multiple suture management members. For instance, the indicia 540 can be a letter, number, etc. and/or have a different color compared to a remainder of the base 492 or support assembly 490. This color can be similar to a colored region R of the suture S, the color of the suture management member, and/or the color of the indicia associated with the suture management member so that the medical professional can associate similarly colored sutures, suture management members, and/or support assemblies, thereby organizing the sutures, suture management members, and support assemblies. In addition, when multiple suture assemblies are included in a kit, such as the kit 700 illustrated in FIG. 27, with the suture handling device, such as a knot pusher or knot pusher/suture trimmer, the suture management member, and/or the devices used to position the sutures, each support assembly can be differently colored. For instance, the indicia for each support assembly can be different and/or the suture management members themselves can be differently colored to indicate a sequence of use so that a medical professional can identify which sutures are associated with which suture management member and so manipulate the support assembly, the suture management members, and associated sutures, in a particular order.

Figure 20:
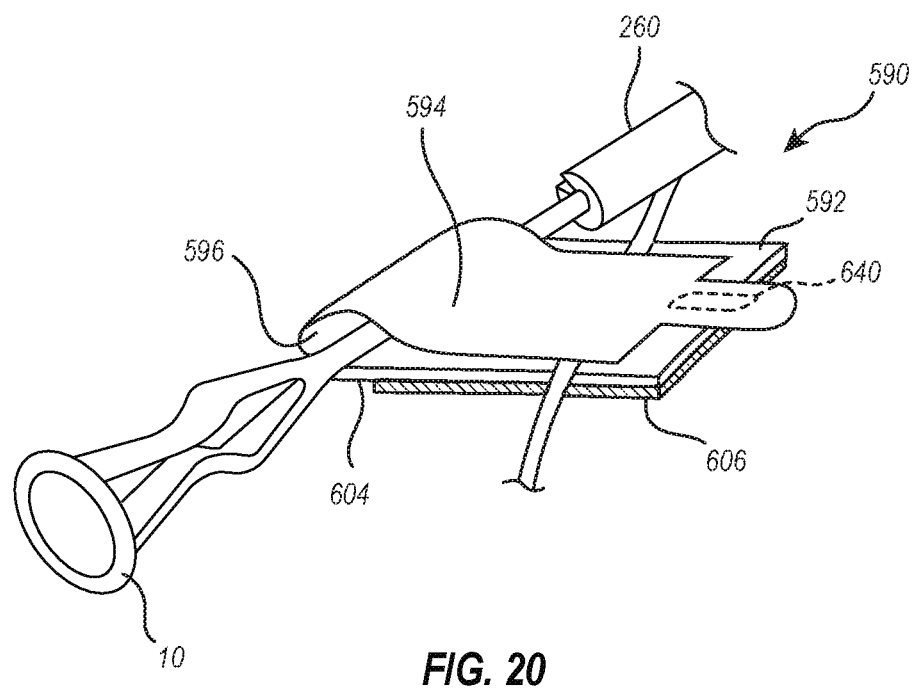
FIG. 20 is a perspective view of another support assembly according to an embodiment of the present invention.
Figure 21:
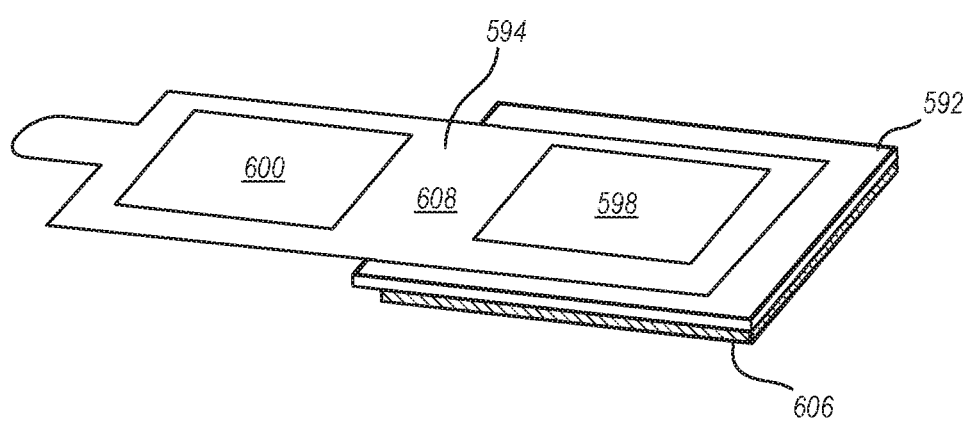
FIG. 21 is another perspective view of the support assembly of FIG. 20, with the closure member in an open configuration according to an embodiment of the present invention.

Turning to FIGS. 20-21, illustrated is an alternate configuration of a support assembly that can support a knot pusher and a suture management member and aid with securing the suture loops relative to an incision or a surgical site. The discussion related to the support assembly 90, 190, 290, 390, and 490 is also applicable to the support assembly 590, wherein like elements are referenced with like reference numerals. Further, the features, functions, and elements described in relation to each of the support assemblies may be combinable with features, functions, and elements described in relation to any other the support assembly.

As illustrated in FIGS. 20-21, a support assembly 590 according to one configuration includes a base 592, such as a mounting portion. From which extends a closure member 594, such as a securing portion. The base 592 couples to a support, such as the surgical drape 84 (FIG. 9), through a coupling structure 606 mounted to a lower surface 604. For instance, the coupling structure 606 can be an adhesive strip on the bottom of the base 592. The adhesive strip can include a peel-away portion that can be removed to expose the adhesive for bonding or coupling to the support. Alternatively, the coupling structure 606 can include hook and loop fasteners, complementary detents, clips, studs, pins, etc.

The closure member 594 is an elongated member that can be folded back upon itself to selectively retain a portion of the knot pusher 10, and/or the suture management member 260, for example, within a channel 596. Two complementary closure portions 598 and 600 formed on an inner surface 608 maintain the closure member 594 in the closed configuration when they cooperate. For instance, the closure portions 598 and 600 can form a hook portion and loop portion of hook and loop fastener material, such as VELCRO. Placing the knot pusher 10 in contact with the inner surface 608, and then using a tab 602 to wrap the closure member 594 around the knot pusher 10, secures the knot pusher 10 when the closure portion 598 and 600 operatively mesh.

The closure member 594 can be flexible or resiliently deformable to accommodate the elongated member 16 of the knot pusher 10, and/or the suture management member, within the channel 596. For instance, in one configuration, the closure member 594 can elongate as the tab 602 positions the closure portions 698 and 600 in cooperative engagement with the hook portion and loop portion meshing. The resiliency to elongation applies a force on the knot pusher 10 to enhance knot pusher restraint. Alternatively, the closure member 594 is resistant to elongation, with only the cooperative engagement of the closure portions 598 and 600 maintaining the knot pusher 10 within the channel 596.

The support assembly 590 can be constructed from a variety of materials. For instance, the base and closure member can be constructed from a polymer, stainless steel, or other materials or combinations thereof, so long as the material provides (i) the base with a desired rigidity or flexibility based upon the support to which is attached by the coupling structure 606 and (ii) the closure member with the desired rigidity or flexibility to receive and accommodate the elongated member and/or the suture management member as described herein. It will be understood, that the materials forming the base and arms need not be the same, but can be if the identified functions can be achieved through the material, configuration of the base and/or arm, or through a combination of both function and configuration.

In addition, the base 692, or more generally, the support assembly 590 can include indicia 640 that provides information to the medical professional for use of multiple suture management members. For instance, the indicia 640 can be a letter, number, etc. and/or have a different color compared to a remainder of the base 692 or support assembly 690. This color can be similar to a colored region R of the suture S, the color of the suture management member, and/or the color of the indicia associated with the suture management member so that the medical professional can associate similarly colored sutures, suture management members, and/or support assemblies, thereby organizing the sutures, suture management members, and support assemblies. In addition, when multiple suture assemblies are included in a kit, such as the kit 700 illustrated in FIG. 27, with the suture handling device, such as a knot pusher or knot pusher/suture trimmer, the suture management member, and/or the devices used to position the sutures, each support assembly can be differently colored. For instance, the indicia for each support assembly can be different and/or the suture management members themselves can be differently colored to indicate a sequence of use so that a medical professional can identify which sutures are associated with which suture management member and so manipulate the support assembly, the suture management members, and associated sutures, in a particular order.

Referring now to FIGS. 22-26, illustrated is the knot pusher 10 and suture management member 60 in accordance with the present invention in use. While reference is made to the knot pusher 10 in the following method, it will be understood that the described method can also be performed using the knot pusher/suture trimmer 110.

Figure 22:
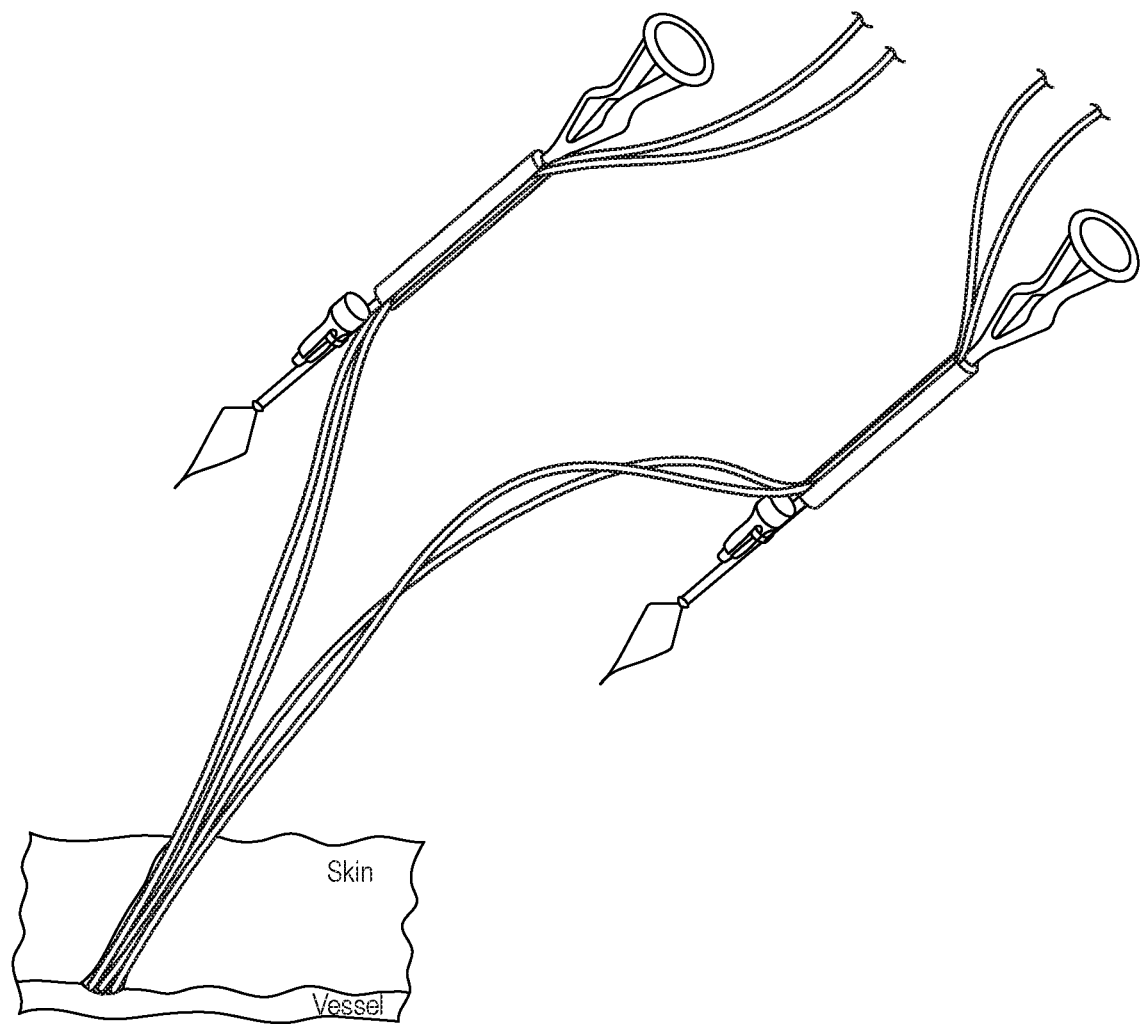
FIG. 22 is an isometric view of two apparatuses in accordance with the present invention, wherein two free suture end portions are coupled to each of the two apparatuses using the suture management member of the present invention.

As shown in FIG. 22, two suture loops have been formed in a vessel wall of a patient, the vessel wall having an opening, or arteriotomy, as a result of a medical procedure, for example. The end portions of the suture loop, those end portions forming the rail and tail used to form the knot, are supported by the suture management member 60 mounted to the knot pusher 10. As illustrated, there are two knot pushers 10*a*, 10*b*, with two suture management members 60*a*, 60*b*. FIG. 22 illustrates a situation following removal of the knot pushers and the suture management members from support assemblies where they were stored until completion of the intravascular procedure. A medical professional is now ready to close the opening or arteriotomy in the vessel V.

The following discussion will reference only one of the two suture management members 60*a*, bob, the knot pushers 10*a*, 10*b*, and the sutures S, S'. However, a similar discussion can also be provided for the other of the suture management members, knot pushers, and sutures.

With continued reference to FIG. 22, the suture S is disposed between the suture management member 260 and the elongated member 16 of the knot pusher 10*a*. By drawing the suture S through the suture-receiving recess 274 or from an end of the body, the medical professional can form a knot that will be subsequently advanced toward the opening or arteriotomy.

Figure 23:
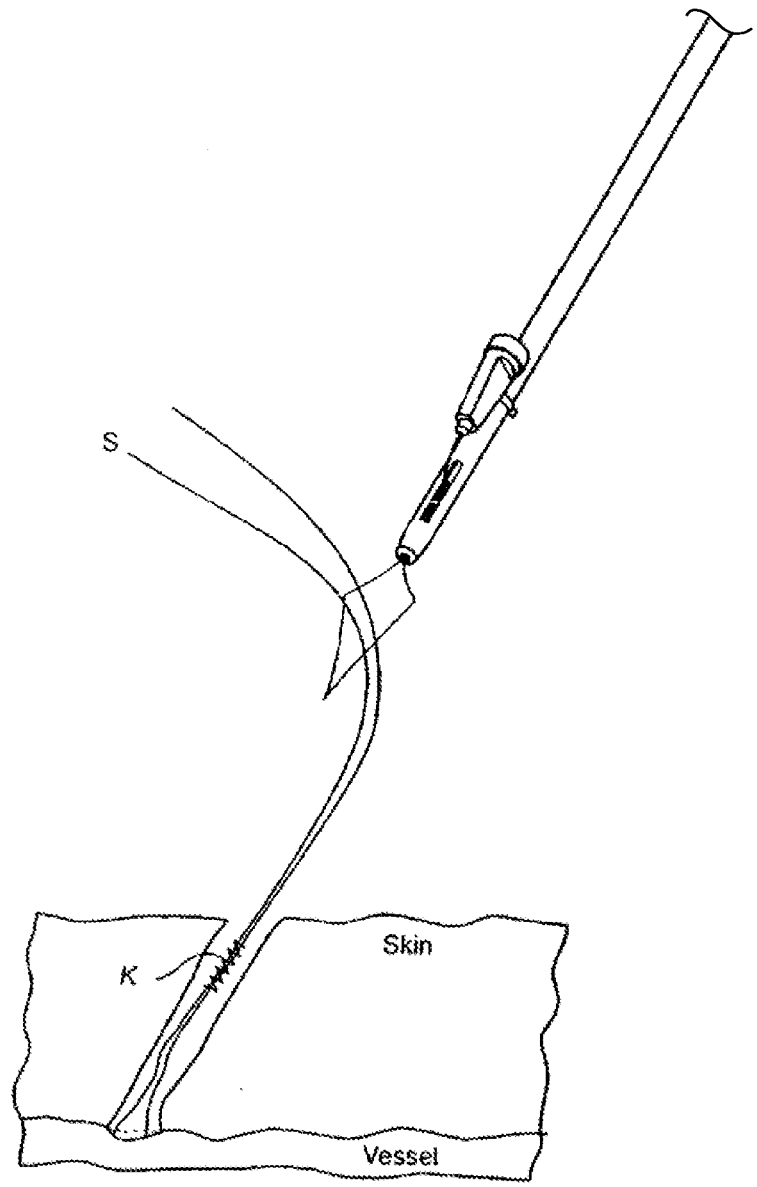
FIG. 23 is an isometric view of one of the two apparatus of FIG. 22, wherein two free suture portions are disposed through the suture snare.
Figure 24:
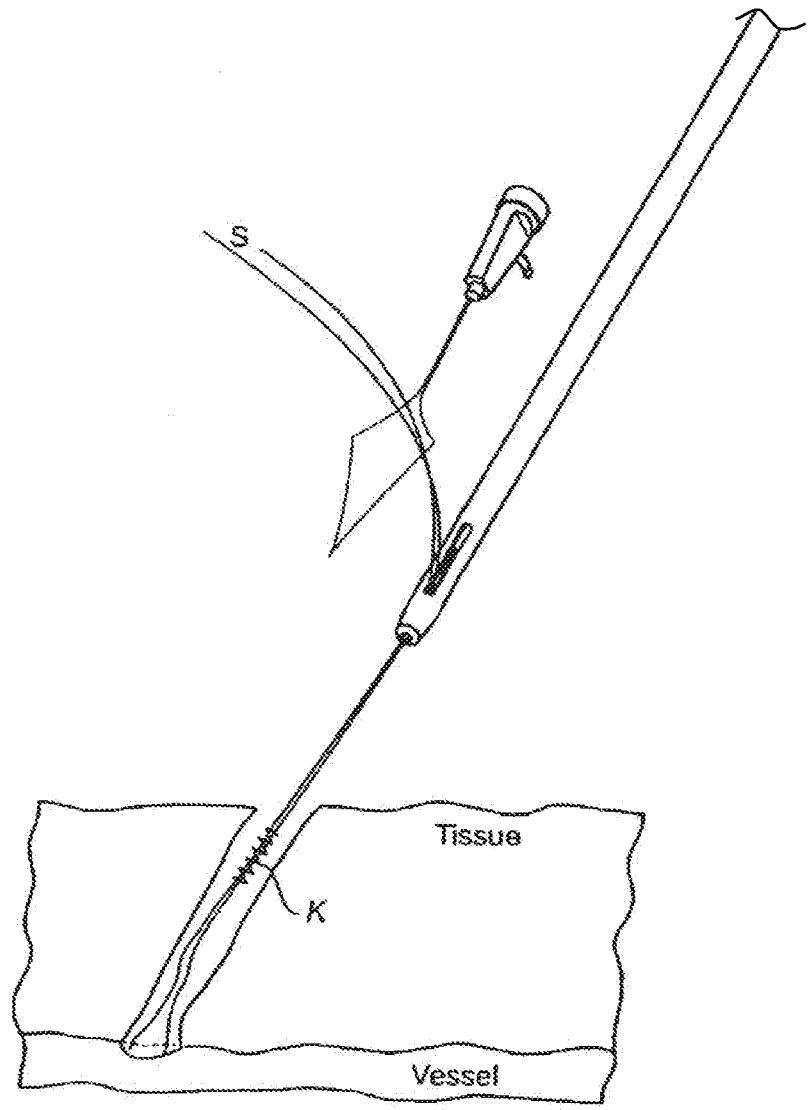
FIG. 24 is an isometric view of the apparatus in accordance with the present invention illustrating the two free suture portions extend through an opening formed in the elongated member of the suture handling device.

With the knot in place, and with reference to FIG. 23, the two free end portions of the suture S are placed within the distal end tip 56 of the snare 54, wherein the distal end tip 56 of the snare 54 has been disposed through the proximal slot 24, the lumen 28 to extent from the aperture 26. The housing 52 being detachably mounted to the elongated member 16 of the knot pusher 10 is removed from the elongated member 16 and using a free hand the distal end of the snare 54 is drawn through the aperture 26, the lumen 28, and from the proximal slot 24. As the snare 54 is drawn through aperture 26 and proximal slot 24, the free end portions of the suture S are additionally drawn through as shown in FIG. 24.

Figure 25:
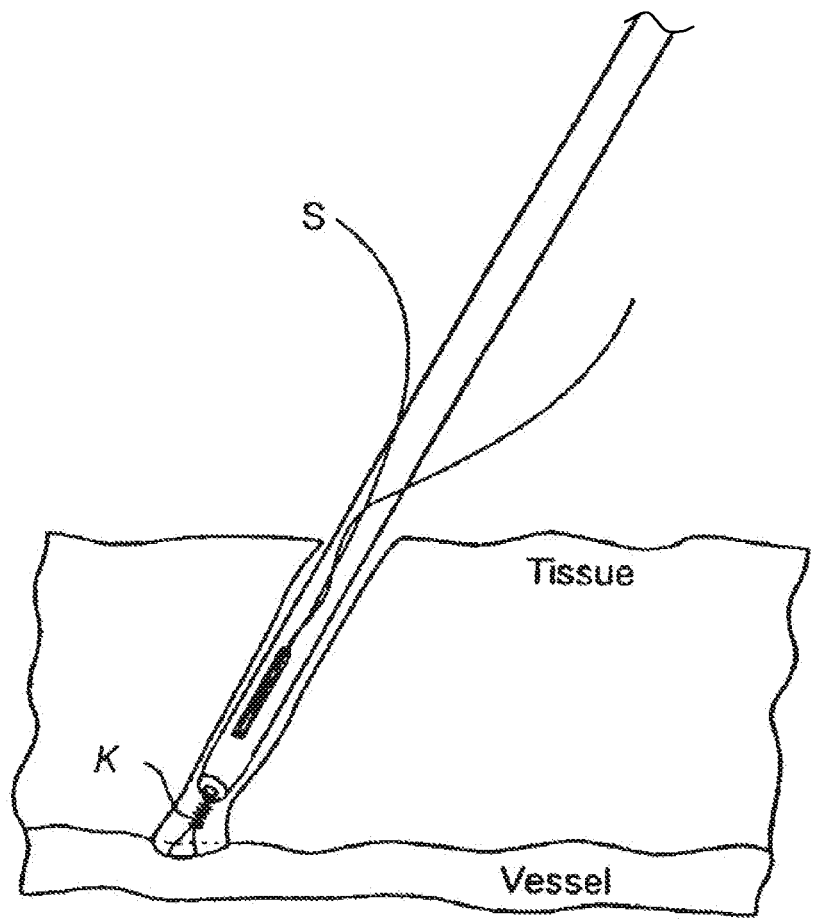
FIG. 25 is an isometric view of the apparatus according to the present invention wherein the distal end of the apparatus is being utilized to advance at least one knot formed in the two free portions of the suture.

Referring now to FIG. 25, there is shown the end portion of the knot pusher 10 placed against the knot K, wherein the knot is then advanced to the wound. One free end of the suture S is held tight to withdraw slack from the suture loop. The end portion of the knot pusher 10 is used to place the knot K tightly against the tissue. After the knot K has been placed, the second free end of the suture S is tensioned, thereby locking the knot K.

Figure 26:
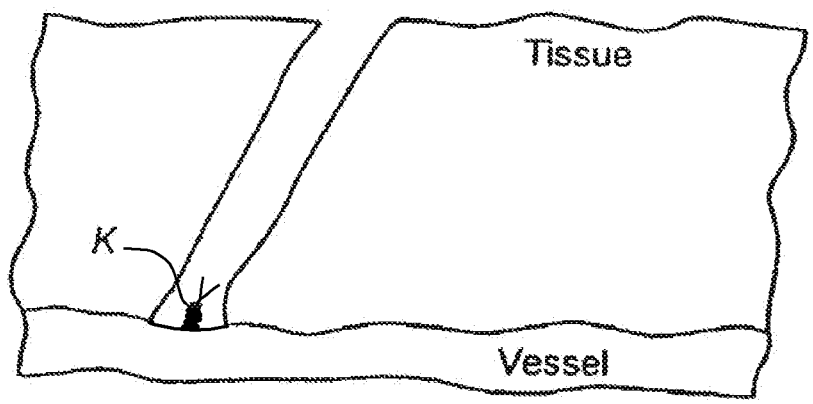
FIG. 26 is an isometric view of the apparatus in accordance with the present invention wherein the two free portions of the suture are cut, and the surgical site is closed.

Following positioning the knot K, suture S is trimmed and the knot pusher 10 removed, as illustrated in FIG. 26. Alternatively, when the knot pusher 110 is used, the ends of the suture S can be cut using the cutting member 130. The surgeon then applies a force to the distal end of the actuating device. The applied force is transmitted through the actuating device to advance the cutting member from a retracted position within the shaft to an extended position as shown. The two free end portions of the suture are then severed by the sharpened distal tip 61 of the cutting member 60 when the distal tip 61 of the cutting member contacts the fitting 50 distal the opening 23. The suture trimmer and the excess suture is then withdrawn from the tissue path, sheath, or cannula thereby leaving a suture loop having a knot and shortened suture tips extending from the knots. It is contemplated that the trimmed suture tail will have a length of about 1 mm to about 10 mm, more preferably between about 3 ram and about 7 mm is preferred to minimize the risks associated with lengths of suture that remain within the body as described above.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A kit comprising:
a plurality of suture handling devices, each suture handling device comprising an elongate member with a distal end and a proximal end, the proximal end comprises a through-aperture that passes through the proximal end in a direction transverse to a longitudinal axis of the elongate member;
a plurality of suture management members, each suture management member being associated with one of the plurality of suture handling devices and being selectively received within the through-aperture, a first portion of the suture management member being deformed by the suture handing device upon being received within the through-aperture while a second portion of the suture management member extends transversely to the longitudinal axis of the elongate member.

2. The kit of claim 1, further comprising a plurality of support assemblies, each support assembly being configured to receive one of the plurality of suture handling devices.

3. The kit of claim 1, further comprising a plurality of support assemblies, each support assembly being configured to receive one of the plurality of suture handling devices and the plurality of suture management members.

4. The kit of claim 1, wherein one suture management member of the plurality of suture management members comprises a suture-receiving recess extending partially through a body and separating the body into a first portion and a second portion, the first portion being biased towards the second portion.

5. The kit of claim 4, wherein the body is monolithic.

6. The kit of claim 4, wherein the body is resiliently deformable.

7. The kit of claim 4, wherein the body comprises a concave portion.

8. The kit of claim 7, wherein the suture-receiving recess is disposed in a transition end of the body, the transition end being pinched by legs that form the through-aperture of the suture handling device.

9. The kit of claim 4, wherein the suture-receiving recess comprises suture retention features configured to selectively engage and retain a suture disposed within the suture-receiving recess.

10. The kit of claim 4, further comprising a groove disposed on an opposite side of the body from the suture-receiving recess.

11. The kit of claim 1, further comprising at least one support assembly selectively coupled to at least one of the suture handling devices, the support assembly comprising a mounting portion and a securing portion.

12. The kit of claim 11, wherein the securing portion comprises an elongate member that can be folded back upon itself.

13. The kit of claim 12, wherein the elongate member comprises a first closure portion and a second closure portion complementary to the first closure portion, the elongate member at least partially wrapping around a portion of the secure handling device.

14. The kit of claim 13, further comprising indicia indicating an order of use of the support assembly.

15. A kit comprising:
a plurality of suture handling devices, each suture handling device comprising an elongate distal end and a proximal end with a through-aperture;
a plurality of suture management members, each suture management member being associated with one of the plurality of suture handling devices and being selectively received within the through-aperture; and
at least one support assembly selectively coupled to at least one of the suture handling devices, the support assembly comprising a mounting portion and a securing portion, the securing portion comprising an elongate member that can be folded back upon itself.

16. The kit of claim 15, wherein the elongate member comprises a first closure portion and a second closure portion complementary to the first closure portion, the elongate member at least partially wrapping around a portion of the secure handling device.

17. The kit of claim 16, further comprising indicia indicating an order of use of the support assembly.

* * * * *